United States Patent [19]
Himmelsbach et al.

[11] Patent Number: 5,922,763
[45] Date of Patent: Jul. 13, 1999

[54] BIPHENYL DERIVATIVES, PHARMACEUTICAL COMPOSITIONS CONTAINING THESE COMPOUNDS AND PROCESSES FOR PREPARING THEM

[75] Inventors: Frank Himmelsbach, Mittelbiberach; Helmut Pieper; Volkhard Austel, both of Biberach; Günter Linz, Mittelbiberach; Thomas Müller, Biberach; Wolfgang Eisert, Biberach; Johannes Weisenberger, Biberach, all of Germany

[73] Assignee: Dr. Karl Thomae GmbH, Biberach an der Riss, Germany

[21] Appl. No.: 08/978,739

[22] Filed: Nov. 26, 1997

Related U.S. Application Data

[62] Division of application No. 08/691,107, Aug. 1, 1996, Pat. No. 5,736,559, which is a division of application No. 08/257,759, May 16, 1994, Pat. No. 5,597,825, which is a continuation of application No. 07/825,246, Jan. 24, 1992, abandoned.

[30] Foreign Application Priority Data

Jan. 24, 1991 [DE] Germany .................. 4102024

[51] Int. Cl.⁶ .......... A61K 31/24; A61K 31/19; C07C 229/34; C07C 251/16
[52] U.S. Cl. ........ 514/534; 514/255; 514/277.8; 514/326; 514/331; 514/381; 514/403; 514/506; 514/570; 544/252; 544/539; 544/569; 546/210; 546/226; 546/230; 546/231; 548/252; 548/539; 548/569; 560/21; 560/34; 560/35; 562/426; 562/430; 562/439; 562/440
[58] Field of Search ............... 560/35, 34, 21; 562/470, 426, 439, 430; 514/534, 570, 255, 277.8, 331, 376, 330, 423, 428, 381, 506; 546/226, 210, 230, 231; 544/58.6, 366, 388, 389; 548/539, 252, 569

[56] References Cited

U.S. PATENT DOCUMENTS

| | | | |
|---|---|---|---|
| 3,821,268 | 6/1974 | Diamond et al. | 544/391 |
| 4,639,452 | 1/1987 | Platel et al. | 544/391 |
| 4,661,522 | 4/1987 | Beetz | 514/632 |
| 4,746,737 | 5/1988 | Fujii et al. | 544/388 |
| 5,061,693 | 10/1991 | Nutt | 514/17 |
| 5,084,466 | 1/1992 | Alig | 514/353 |

FOREIGN PATENT DOCUMENTS

| | | |
|---|---|---|
| A248433 | 3/1982 | European Pat. Off. . |
| 3215676 | 11/1982 | Germany . |

OTHER PUBLICATIONS

Marder VJ and Sherry S. The New England Journal of Medicine, 318(23), 1512–20 Jun. 1988.

Frearson PM and Stern ES. J. Chem. Soc., pp. 3062–3064, (CA 53:3219f) 1958.

*Primary Examiner*—Evelyn Mei Huang
*Attorney, Agent, or Firm*—R. P. Raymond; M-E. M. Devlin; A. R. Stempel

[57] ABSTRACT

The invention relates to biphenyl derivatives of general formula

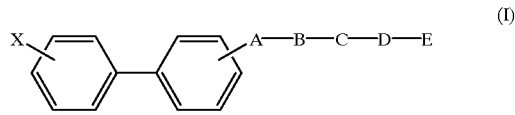

wherein

A to E and X are defined as in claim 1, the stereoisomers thereof, including their mixtures and the salts thereof, particularly the physiologically acceptable salts thereof with inorganic or organic acids or bases, which have valuable properties, preferably aggregation-inhibiting effects, pharmaceutical compositions containing these compounds and processes for preparing them.

9 Claims, No Drawings

BIPHENYL DERIVATIVES, PHARMACEUTICAL COMPOSITIONS CONTAINING THESE COMPOUNDS AND PROCESSES FOR PREPARING THEM

This is a division of application Ser. No. 08/691,107, filed on Aug. 1, 1996(U.S. Pat. No. 5,736,559), which is a division of application Ser. No. 08/257,759, filed May 16, 1994 (issued—U.S. Pat. No. 5,597,825), which is a continuation of application Ser. No. 07/825,246, filed Jan. 24, 1992 (abandoned).

The invention relates to biphenyl derivatives of general formula

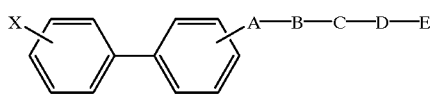
(I)

the stereoisomers thereof, including the mixtures thereof and the salts, particularly the physiologically acceptable salts thereof with inorganic or organic acids or bases, which have valuable properties, especially valuable pharmacological properties, particularly inhibitory effects on aggregation, pharmaceutical compositions containing these compounds and processes for preparing them.

In general formula I above (with the proviso that one of the rings of the biphenyl moiety may be mono- or disubstituted by $R_1$ and the other may be mono- or disubstituted by $R_2$, wherein $R_1$ and $R_2$, which may be identical or different, represent halogen atoms, alkyl, hydroxy, trifluoromethyl, amino, nitro, alkoxy, alkylsulphenyl, alkylsulphinyl, alkylsulphonyl, alkylcarbonylamino, N-alkyl-alkylcarbonylamino, arylcarbonylamino, N-alkyl-arylcarbonylamino, alkylsulphonylamino, N-alkyl-alkylsulphonylamino, arylsulphonylamino or N-alkyl-arylsulphonylamino groups, wherein the aryl moiety may contain a phenyl ring which may be mono-, di- or trisubstituted by halogen atoms, hydroxy, amino, alkyl, alkoxy, alkylsulphenyl, alkylsulphinyl, alkylsulphonyl, alkylcarbonylamino and alkylsulphonylamino groups and the alkyl moiety may contain 1 to 3 carbon atoms, or R, and $R_2$ may each also represent a naphth ring), X represents a cyano group or an amino, aminoalkyl, amidino, guanidino or guanidinoalkyl group, wherein one of the hydrogen atoms at one of the nitrogen atoms may be replaced by a hydroxy, amino or cyano group, by a $C_{1-3}$-alkoxy group, by a $C_{1-4}$-alkyl group, by an alkoxycarbonyl group having a total of 2 to 5 carbon atoms, by a phenylalkoxy-carbonyl group having 1 to 3 carbon atoms in the alkyl moiety, by a phenyloxycarbonyl, benzoyl, alkylcarbonyl or phenylalkylcarbonyl group, wherein the alkyl moiety may contain 1 to 3 carbon atoms and the above-mentioned phenyl groups may be mono- or disubstituted by the above-mentioned groups $R_1$ and $R_2$, A represents a bond, an oxygen or sulphur atom or an $-NR_3-CO-$, $-CO-NR_3-$, $-NR_4-$, $-SO-$, $-SO_2-$, $-CO-$, $-SO_2-NR_3-$, $-NR_3-SO_2-$, $-NR_3-CO-NR_3-$ or $-NR_3-SO_2-NR_3-$ group, B represents a bond, a straight-chained or branched $C_{1-6}$alkylene group which may be mono- or polyunsaturated, whilst a double bond may not be directly linked to an oxygen, sulphur or phosphorus atom of groups A, C or E and a triple bond may not be directly linked to a heteroatom of groups A, C or E, or B may represent a $C_{3-7}$-cycloalkylene group, a phenylene or naphthylene group which may be mono-, di- or trisubstituted in the aromatic nucleus by halogen atoms, amine, hydroxy, $C_{1-3}$-alkyl or $C_{1-3}$-alkoxy groups, C represents a bond, a $-CO-$, $-CO-NR_3-$, $-CO-NR_3-(CH_2)_n-R_5CR_6-$, $-CO-NR_3-(CH_2)_n-NR_5-$ or $-CO-NR_3-(CH_2)_n-CR_5=CH-$ group , or, if a heteroatom of group A is not bound to the same carbon atom of group B as is group C, C may represent an oxygen or sulphur atom, an $-SO-$, $-SO_2-$, $-NR_4-$, $-NR_3-CO-$ or $-NR_3-(CH_2)_n-CHR_5-$ group, whilst generally an oxygen or sulphur atom of group C cannot directly follow an oxygen or sulphur atom or a $-CO-$ group of group A and an oxygen atom or a sulphenyl or sulphinyl group of group C cannot directly follow a nitrogen atom of group A and a $-CO-$ group of group C cannot directly follow an oxygen or sulphur atom or a $-CO-NR_3-$ group of group A, D represents a bond, a straight-chained or branched $C_{1-4}$-alkylene group which may be mono- or polyunsaturated, wherein a double bond may not be bound directly to an oxygen, sulphur or phosphorus atom of groups A, C or E or to a triple bond of group B and a triple bond may not be directly linked to a heteroatom of groups A, C or E or to a double or triple bond of group B, or D may represent a phenylene or ($C_{1-3}$-alkylene)phenylene, whilst the phenylene group may be mono-, di- or trisubstituted by halogen atoms, amino, hydroxy, $C_{1-3}$-alkyl or $C_{1-3}$-alkoxy groups, and E represents a carboxy, sulpho, phosphono, 5-tetrazolyl or O-alkyl-phosphono group having 1 to 3 carbon atoms in the alkyl moiety, an $(R_3)_2NCO-$ group, an $C_{2-6}$ (alkoxycarbonyl) wherein the alkoxy moiety may be substituted in the 1-, 2- or 3-position by a phenyl group (which may be mono- or disubstituted by the above-mentioned groups $R_1$ and $R_2$), by a pyridyl group or in the 2- or 3-position by a pyrrolidino, piperidino, hexamethyleneimino, 2-oxo-1-pyrrolidinyl, morpholino, thiomorpholino, 1-oxidothiomorpholino or 1,1-dioxidothiomorpholino group or by a piperazino group optionally substituted in the 4-position by a group $R_5$, whilst at least one of the groups A, B, C or D does not represent a bond, group E cannot directly follow a heteroatom of groups A or C and, if X represents an aminoalkyl group, the shortest distance between the $NH_2$ group and group E is at least 12 bonds, whilst n represents the number 0, 1 or 2, $R_3$ represents a hydrogen atom or an optionally phenyl-substituted $C_{1-3}$-alkyl group, wherein the phenyl group may be mono- or disubsuituted by the above-mentioned groups $R_1$ and $R_2$.

$R_4$ represents a hydrogen atom, an optionally phenyl-substituted $C_{1-3}$-alkyl group, a formyl group, a carbonyl or sulphonyl group substituted by a $C_{1-3}$-alkyl group, by a phenyl($C_{1-3}$-alkyl) group or by a phenyl group, whilst the phenyl groups may be mono- or disubstituted by the above-mentioned groups $R_1$ and $R_2$, and $R_5$ represents a hydrogen atom or a $C_{1-3}$-alkyl group or a $-CO-NR_3-(C_{1-3}$-alkylene)-phenyl group in which, the phenyl group may be mono- or disubstituted by the above-mentioned groups $R_1$ and $R_2$, and $R_3$ is defined as hereinbefore or, if the group C is substituted by the groups $R_3$ and $R_5$, $R_5$ together with $R_3$ may represent a $C_{2-4}$-alkylene group and $R_6$ represents a hydrogen atom or a hydroxy, carboxyalkyl or alkoxycarbonylalkyl group, wherein the alkyl and alkoxy moieties may each contain 1 to 3 carbon atoms.

Preferred compounds of general formula I above are those wherein, with the proviso that one of the rings of the biphenyl moiety may be substituted by $R_1$ and the other may be substituted by $R_2$, wherein $R_1$ and $R_2$, which may be identical or different, represent fluorine, chlorine or bromine atoms, alkyl, hydroxy, trifluoromethyl, amino, nitro, alkoxy, alkylsulphenyl, alkylsulphinyl, alkylsulphonyl, alkylcarbonylamino, benzoylamino, alkylsulphonylamino or phenylsulphonylamino groups wherein the alkyl and alkoxy moieties may each contain 1 to 3 carbon atoms, or with the proviso that one of the rinqs of the biphenyl moiety may be disubstituted by $R_1$ and the other by $R_2$, wherein $R_1$ and R2 which may be identical or different, represent $C_{,13}$-alkyl groups, chlorine or bromine atoms, X represents a cyano group, an amino($C_{1-3}$-alkyl), an amino, amidino or guanidino group, whilst one of the hydrogen atoms at one of the nitrogen atoms in the above-mentioned groups may be substituted by an amino group, by a $C_{1-4}$-alkyl group, by a $C_{1-3}$-alkoxy, by a $C_{2-5}$ (alkoxycarbonyl) group, or by a benzyloxycarbonyl, 1-phenylethoxycarbonyl, 2-phenylethoxycarbonyl or phenyloxycarbonyl group, A represents a bond, an oxygen or sulphur atom, an —$NR_3$—CO—, —CO—$NR_3$—, —$NR_4$—, —SO—, —$SO_2$—, —CO—, —$SO_2$—$NR_3$—, —$NR_3$—CO—$NR_3$— or —$NR_3$—$SO_2$—$NR_3$— group, B represents a bond, a straight-chained or branched $C_{1-6}$-alkylene group, a $C_{3-5}$-alkenylene or $C_{3-5}$-alkynylene group, whilst a double bond may not be linked directly to an oxygen, sulphur or phosphorus atom of groups A, C or E and a triple bond may not be directly linked to a heteroatom of groups A, C or E, or B may represent a cyclohexylene or phenylene group, C represents a bond, a —CO—$NR_3$—, —CO—$NR_3$—($CH_2$)$_n$—$R_5CR_6$—, —CO—$NR_3$—($CH_2$)$_n$—$NR_5$—, or —CO—$NR_3$—($CH_2$)$_n$—$CR_5$=CH— group, or, if a heteroatom of group A is not bound to the same carbon atom of group B as is group C, C may represent an oxygen or sulphur atom, an —SO—, —$SO_2$—, —$NR_4$—, —$NR_3$—CO— or —$NR_3$—($CH_2$)$_n$—$CHR_5$— group, whilst generally an oxygen or sulphur atom of group C cannot directly follow an oxygen or sulphur atom or a —CO— group of group A, and an oxygen or sulphenyl or sulphinyl group of group C cannot directly follow a nitrogen atom of group A, and a —CO— group of group C cannot directly follow an oxygen or sulphur atom or a —CO—$NR_3$— group of group A, D represents a bond, a straight-chained or branched $C_{1-4}$-alkylene group, a phenylene or ($C_{1-3}$-alkylene) phenylene, and E represents a carboxy, sulpho, phosphono, 5-tetrazolyl or O-alkyl-phosphono group having 1 to 3 carbon atoms in the alkyl moiety, an ($R_3$)$_2$NCO— group, a $C_{2-5}$(alkoxycarbonyl) group wherein the alkoxy moiety may be substituted in the 1-, 2- or 3-position by a phenyl or pyridyl group or the alkoxy moiety may be substituted in the 2- or 3-position by a 2-oxo-1-pyrrolidinyl, morpholino, thiomorpholino or 1-oxido-thiomorpholino group, whilst at least one of the groups A, B, C or D does not represent a bond, group E cannot directly follow a heteroatom of group A or C and, if X represents an aminoalkyl group, the shortest distance between the $NH_2$ group and group E is at least 12 bonds, wherein n represents the number 0, 1 or 2, $R_3$ represents a hydrogen atom or a $C_{1-3}$-alkyl group, $R_4$ represents a hydrogen atom, a $C_{1-3}$-alkyl group, a carbonyl or sulphonyl group substituted by a $C_{1-3}$-alkyl group or by a phenyl group, and $R_5$ represents a hydrogen atom or a $C_{1-3}$-alkyl group or a —CO—$NR_3$—($C_{1-3}$-alkylene)-phenyl group wherein the phenyl moiety may be substituted by one or two $C_{1-3}$-alkoxy groups and $R_3$ is defined as hereinbefore, or, if the group C is substituted by the groups $R_3$ and $R_5$, $R_5$ together with $R_3$ may represent a $C_{2-4}$-alkylene group, and $R_6$ may represent a hydrogen atom or a hydroxy, carboxyalkyl or alkoxycarbonylalkyl group, wherein the alkyl and alkoxy moieties may each contain 1 to 3 carbon atoms, the stereoisomers thereof, including the mixtures and the salts thereof.

Particularly preferred compounds of general formula I above are those wherein the phenyl group linked to the group X may be substituted by a fluorine, chlorine or bromine atom, the phenyl ring linked to the group A may be substituted by a fluorine or chlorine atom or by a hydroxy, methoxy, trifluoromethyl, methylsulphenyl, methylsulphinyl, methylsulphonyl, nitro, amino, acetylamino, benzoylamino, methanesulphonylamino or benzenesulphonyl-amino group or the phenyl ring linked to group A may be substituted by one or two methyl groups or by one or two bromine atoms, X represents an aminomethyl, amidino or guanidino group wherein a hydrogen atom at one of the nitrogen atoms may be replaced by a $C_{1-4}$-alkyl group, or by a methoxycarbonyl, ethoxycarbonyl or benzyloxycarbonyl group, A represents a bond, an oxygen or sulphur atom, an —NH—CO—, —$NCH_3$—CO—, —CO—NH—, —CO—$NCH_3$—, —$NCH_3$, —SO—, —$SO_2$—, —$SO_2$—NH—, —$SO_2$—$NCH_3$—, —CO—, —NH—CO—NH—, —NH—$SO_2$—NH—or —$NCH_3$—CO—$NCH_3$— group, B represents a bond, a straight-chained or branched $C_{1-5}$-alkylene group, a straight-chained or branched $C_3$-alkenylene group in which the double bond cannot be directly linked to an oxygen, sulphur or phosphorus atom of groups A, C or E, or B may represent a cyclohexylene or phenylene group, C represents a bond, a —CO—NH—, —CO—$NCH_3$, —CO—NH—($CH_2$)$_2$—CH($CH_2$—COOH)—, —CO—$NCH_3$—($CH_2$)$_2$—CH($CH_2$—COOH)—, —CO—NH—($CH_2$)$_2$—CH($CH_2$—COO$CH_3$)—, —CO—$NCH_3$—($CH_2$)$_2$—CH($CH_2$—COO$CH_3$)—, pyrrolidinylene-N-carbonyl, piperidinylene-N-carbonyl, piperazinylene-N-carbonyl or 4-methanylylidene-piperidinocarbonyl group wherein the group —D—E is bound to the methanylylidene group, a 4-hydroxy-4-piperidinylene-N-carbonyl, 4-carboxymethyl-4-piperidinylene-N-carbonyl or 4-methoxycarbonylmethyl-4-piperidinylene-N-carbonyl group wherein the group —D—E is bound to the 4-position, or a [[[2-(methoxyphenyl)-ethyl]-aminocarbonyl]-methylene]-aminocarbonyl group wherein the group —D—E is bound to the methylene carbon atom, or, if a heteroatom of group A is not bound to the same carbon atom of group B as is group C, C may represent an oxygen or sulphur atom, an —SO—, —$SO_2$—, —NH—, —$NCH_3$—, —N(CO$CH_3$)—, —N(benzoyl)—, —N($SO_2CH_3$)—, —NH—CO—, 1-pyrrolidinylene or 1-piperidinylene group, whilst generally an oxygen or sulphur atom of group C cannot directly follow an oxygen or sulphur atom or a —CO— group of group A, and an oxygen or sulphenyl or sulphinyl group of group C cannot directly follow a nitrogen atom of group A, and a —CO— group of group C cannot directly follow an oxygen or sulphur atom or a —CO—NH— or —CO—$NCH_3$— group of group A, D represents a bond, a straight-chained or branched $C_{1-3}$-alkylene group or a ($C_{1-2}$-alkylene)phenylene group, and E represents a carboxy, sulpho, phosphono, 5-tetrazolyl or O-methyl-phosphono group, a $C_{2-5}$(alkoxycarbonyl) group wherein the alkoxy moiety may be substituted in the 1- or 2-position by a phenyl group, or E may represent an aminocarbonyl, methylaminocarbonyl or dimethylaminocarbonyl group, whilst at least one of the groups A, B, C or D does not represent a bond, group E cannot directly follow a heteroatom of groups A or C and, if X represents an aminomethyl group, the shortest distance between the amino group and group E is at least 12 bonds, the stereoisomers thereof, including the mixtures and salts thereof.

However, most particularly preferred compounds of general formula I are those wherein the phenyl ring connected to the group X is unsubstituted and the phenyl ring connected to the group A may be substituted by a hydroxy or methoxy group, X represents an aminomethyl or amidino group in which a hydrogen atom at one of the nitrogen atoms may be replaced by a methoxycarbonyl, ethoxycarbonyl or benzyloxycarbonyl group, A represents a bond, an oxygen atom, an —NH—CO—, —CO—NH—, —CO—NCH$_3$—, —SO$_2$—NH— or —NH—SO$_2$—NH— group, B represents a bond, a straight-chained $C_{1-5}$-alkylene group, a cyclohexylene or phenylene group, C represents a bond or, if C does not directly follow an oxygen or sulphur atom or a —CO—NH— or —CO—NCH$_3$— group of group A, C may represent a —CO—NH— group, a piperidinylene-N-carbonyl group linked in the 3- or 4-position to group —D—E, a 4-piperazinylene-N-carbonyl or 4-methanylylidene-piperidinocarbonyl group wherein the group —D—E is bound to the methanylylidene group, or C may represent a 4-hydroxy-4-piperidinylene-N-carbonyl, 4-carboxymethyl-4-piperidinylene-N-carbonyl or 4-methoxycarbonylmethylene-piperidinylene-N-carbonyl group wherein the group —D—E is bound to the 4-position, or C may represent a [[[2-(4-methoxyphenyl)-ethyl] aminocarbonyl]-methylene]-aminocarbonyl group wherein the group —D—E is linked to the methylene carbon atom, or, if C does not directly follow an oxygen atom or a carbonyl group of group A and a heteroatom of group A is not linked to the same carbon atom of B which carries the group C, C may also represent an —NH—CO— group or, if C does not directly follow an oxygen atom of group A and a heteroatom of group A is not linked to the same carbon atom of B which carries group C, C may also represent a 1-piperidinylene group, D represents a bond, a methylene, ethylene, methylenephenylene or ethylenephenylene group and p E represents a carboxyl, methoxycarbonyl, ethoxycarbonyl, benzyloxycarbonyl, aminocarbonyl, dimethylaminocarbonyl or 5-tetrazolyl group, whilst at least one of the groups A, B, C or D does not represent a bond and E cannot directly follow a heteroatom of groups A or C, and, if X represents an aminomethyl group, the shortest distance between the amino group and group E is at least 12 bonds, particularly those compounds of general formula I wherein the biphenylyl group is unsubstituted, X is an aminomethyl or amidino group in which a hydrogen atom at one of the nitrogen atoms may be replaced by a methoxycarbonyl or benzyloxycarbonyl group, A represents a bond, an oxygen atom, an —NH—CO— or —CO—NH— group, B represents a bond, a straight-chained $C_{1-5}$-alkylene group or a cyclohexylene group, C represents a bond or, if C does not directly follow a heteroatom or a carbonyl group of group A, C may represent a —CO—NH— group, a piperidinylene-N-carbonyl group linked in the 3- or 4-position to group —D—E, a piperazinylene-N-carbonyl group wherein group —D—E is bound to the 4-position, or a [[[2-(4-methoxyphenyl)-ethyl)]-aminoco-itonyl] -methylene) -aminocarbonyl group wherein the group —D—E is linked to the methylene carbon atom, D represents a bond, a methylene or ethylene group and E represents a carboxyl, methoxycarbonyl, ethoxycarbonyl or benzyloxycarbonyl group whilst at least one of the groups A, B, C or D does not represent a bond and E cannot directly follow a heteroatom of groups A or C, and if X represents an aminomethyl group the shortest distance between the amino group and the group E is at least 12 bonds, the stereoisomers, including the mixtures thereof and the salts thereof.

According to the invention, the new compounds of general formula I may be obtained, for example, by the following methods which are known per se:

a) in order to prepare compounds of general formula I wherein X contains an amidino group:

Reacting a compound of general formula

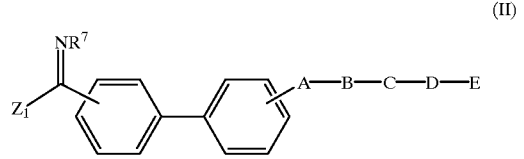

optionally formed in the reaction mixture, wherein A, B, C, D and E are defined as hereinbefore, $R_7$ represents a hydrogen atom or a $C_{1-4}$- alkyl group and $Z_1$ represents an alkoxy or aralkoxy group such as a methoxy, ethoxy, n-propoxy, isopropoxy or benzyloxy group or an alkylthio or aralkylthio group such as a methylthio, ethylthio, n-propylthio or benzylthio group or an amino group, with an amino of general formula $$NH_2—R_8 \tag{III}$$

wherein $R_8$ represents a hydrogen atom, a $C_{1-4}$-alkyl group, a hydroxy group, a $C_{1-3}$-alkoxy group or an amino group, or with the acid addition salts thereof.

The reaction is expediently carried out in a solvent such as methanol, ethanol, n-propanol, water, methanol/water, tetrahydrofuran or dioxane at temperatures between 0 and 150° C., preferably at temperatures between 20 and 120° C., with a corresponding free amine or with a corresponding acid addition salt such as ammonium carbonate.

A compound of general formula II may be obtained, for example, by reacting a corresponding nitrile with a suitable alcohol such as methanol, ethanol, n-propanol, isopropanol or benzyl alcohol in the presence of an acid such as hydrochloric acid or by reacting a corresponding amide with a trialkyloxonium salt such as triethyloxoniumtetrafluoroborate in a solvent such as methylene chloride, tetrahydrofuran or dioxane at temperatures between 0 and 50° C., but preferably at 20° C., or a corresponding nitrile with hydrogen sulphide, appropriately in a solvent such as pyridine or dimethylformamide and in the presence of a base such as triethylamine with subsequent alkylation of the resulting thioamide with a suitable alkyl or aralkyl halide.
b) In order to prepare compounds of general formula I wherein X represents an aminomethylene group:
Reduction of a compound of general formula

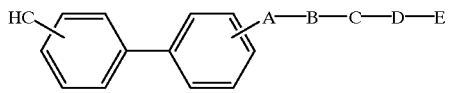
(IV)

wherein
A, B, C, D and E are defined as hereinbefore.

The reduction is preferably carried out in a suitable solvent such as methanol, methanol/water, methanol/water/ammonia, ethanol, ether, tetrahydrofuran, dioxane or dimethylformamide in the presence of catalytically activated hydrogen, e.g. hydrogen in the presence of Raney nickel, platinum or palladium/charcoal, or in the presence of a metal hydride such as sodium borohydride, lithium borohydride or lithium aluminum hydride at temperatures between 0 and 100° C., preferably at temperatures between 20 and 80° C.
c) In order to prepare compounds of general formula I wherein X represents a guanidino group:
Reacting a compound of general formula

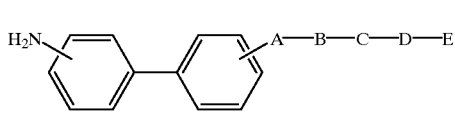
(V)

wherein
A, B, C, D and E are defined as hereinbefore, or an acid addition salt thereof, with cyanamide.

The reaction is appropriately carried out in a solvent such as dioxane, dioxane/water or tetrahydrofuran, preferably at temperatures between 60 and 120° C., e.g. at the boiling temperature of the reaction mixture.
d) In order to prepare compounds of general formula I wherein E represents a carboxyl group:
Converting a compound of generel formula

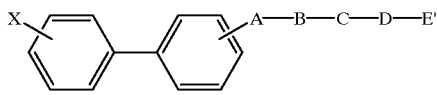
(VI)

wherein
A, B, C, D and X are defined as hereinbefore and E', which is bound to a carbon atom, represents a group which can be converted by hydrolysis, treatment with acids, thermolysis or hydrogenolysis into a carboxyl- or bis-(hydroxycarbonyl)methyl group, optionally with subsequent decarboxylation.

For example, functional derivatives of the carboxyl group such as unsubstituted or substituted amides, esters, thioesters, trimethylsilylesters, orthoesters, iminoesters, amidines or anhydrides, or a nitrile group may be converted by hydrolysis into a carboxyl group, esters with tertiary alcohols, e.g. tert.butylesters, may be converted by treatment with an acid or thermolysis into a carboxyl group and esters with aralkanols, e.g. benzylesters, may be converted by hydrogenolysis into a carboxyl group.

The hydrolysis is appropriately carried out either in the presence of an acid such as hydrochloric, sulphuric, phosphoric, trichloroacetic or trifluoroacetic acid, in the presence of a base such as lithium hydroxide, sodium hydroxide or potassium hydroxide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture. When treating with an organic acid such as trichloroacetic or trifluoroacetic acid, any alcoholic hydroxy groups present may simultaneously be converted into a corresponding acyloxy group such as a trifluoroacetoxy group.

If E' is a compound of formula VI represents a cyano or aminocarbonyl group, these groups may also be converted into a carboxyl group with a nitrite, e.g. sodium nitrite, in the presence of an acid such as sulphuric acid, which may appropriately be used as the solvent at the same time, at temperatures between 0 and 50° C.

If E' in a compound of formula VI represents a tert.butyloxycarbonyl group, for example, the tert.butyl group may also be cleaved by treating with an acid such as trifluoroacetic acid, formic acid, p-toluenesulphonic acid, sulphuric acid, phosphoric acid or polyphosphoric acid, optionally in an inert solvent such as methylene chloride, chloroform, benzene, toluene, tetrahydrofuran or dioxane, preferably at temperatures between −10° C. and 120° C., e.g. at temperatures between 0 and 60° C., or thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 100° C.

If E' in a compound of formula VI represents a benzyloxycarbonyl group, for example, the benzyl group may also be hydrogenolytically cleaved in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0 and 50° C., e.g. at ambient temperature, under a hydrogen pressure of 1 to 5 bar. During hydrogenolysis, other groups may also be reduced at the same time, e.g. a nitro group may be reduced to an amino group or a benzyloxy group to a hydroxy group.

The subsequent decarboxylation which may be required is preferably carried out in a solvent such as glacial acetic acid el evated temperatures, e.g. at the boiling temperature of the reaction mixture.
e) In order to prepare compounds of general formula I wherein A represents an —NR$_3$—CO—, —CO—NR$_3$—, —SO$_2$—NR$_3$— or —NR$_3$—SO$_2$— group:
Reacting a compound of general formula

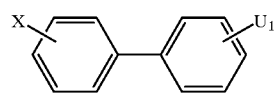
(VII)

with a compound of general formula

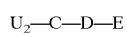      (VIII)

wherein
C, D, E and X are defined as hereinbefore, one of the groups U$_1$ or U, represents an HNR$_3$— group, wherein $R_3$ is defined as hereinbefore, and the other group $U_1$ or $U_2$ represents a $Z_2$—A'— group, wherein A' represents a carbonyl or sulphonyl group and $Z_2$ represents a hydroxy group or a nucleophilic leaving group such as a halogen atom, an alkoxy, aralkoxy, aryloxy, alkylthio, arylthio or alkoxycarbonyloxy group, e.g. a chlorine, bromine or iodine atom, a methoxy, ethoxy, benzyloxy, phenoxy, methylthio, phenylthio or isobutyloxy-carbonyloxy group, or with the reactive derivatives thereof such as the internal anhydrides thereof.

The reaction is conveniently carried out in a solvent such as methanol, methylene chloride, chloroform, carbon tetrachloride, ether, tetrahydrofuran, dioxane, benzene, toluene, acetonitrile, dimethylsulphoxide, sulpholane or dimethylformamide, optionally in the presence of an inorganic or organic base, optionally in the presence of a reaction accelerator such as 4-dimethylamino-pyridine, copper or copper(I)chloride or, if $Z_2$ represents a hydroxy group, optionally in the presence of an acid-activating agent such as N,N'-carbonyldiimidazole or N,N'-dicyclohexylcarbodiimide, optionally in the presence of hydroxybenztriazole or hydroxysuccinimide or optionally in the presence of a dehydrating agent or optionally in the presence of an agent which activates the amino group, at temperatures between −20 and 200° C., but preferably at temperatures between −10 and 160° C.

f) In order to prepare compounds of general formula I wherein the E—D—C group is an HOOC—$(CH_2)_n$—CO—NH— group:

Hydrolysis of a compound of general formula

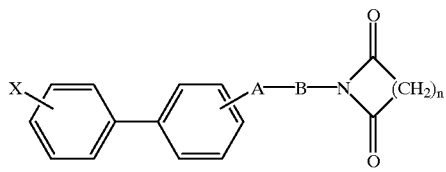
(IX)

wherein

A, B, X and n are defined as hereinbefore.

The hydrolysis is conveniently carried out in the presence of a base such as sodium hydroxide or potassium hydroxide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture.

g) In order to prepare compounds of general formula I wherein E represents a $C_{2-6}$(alkoxycarbonyl) group wherein the alkoxy moiety may be substituted in the 1-, 2- or 3-position by an aryl or pyridyl grolip or may be substituted in the 2- or 3-position by a pyrrolidino, piperidino, hexamethylene-imino, 2-oxo-1-pyrrolidinyl, morpholino, thiomorpholino or 1,1-dioxido-thiomorpholino group or by a piperazino group optionally substituted in the 4-position by a group $R_5$:

Reacting a compound of general formula

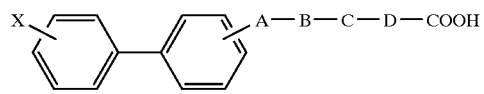
(X)

wherein

A, B, C, D and X are defined as hereinbefore, or the reactive derivatives thereof such as the esters, anhydrides or halides thereof, with a compound of general formula

H—$R_9$ (XI)

wherein $R_9$ represents a $C_{1-5}$-alkoxy group wherein the alkoxy moiety may be substituted in the 1-, 2- or 3-position by an aryl or pyridyl group or in the 2- or 3-position by a pyrrolidino, piperidino, hexamethyleneimino, 2-oxo-1-pyrrolidinyl, morpholino, thiomorpholino or 1,1-dioxidothiomorpholino group or by a piperazino group optionally substituted in the 4-position by a group $R_5$.

The reaction is conveniently carried out in a solvent such as tetrahydrofuran, chloroform, dimethylformamide or in a corresponding alcohol in the presence of an acid activating agent or a dehydrating agent, e.g. in the presence of isobutylchloroformate, thionyl chloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benztriazole, N,N'-carbonyldiimidazole or N,N'-thionyldiimidazole or triphenylphosphine/carbon tetrachloride, or an agent which activates the amino group, e.g. phosphorus trichloride, and optionally in the presence of a base such as sodium carbonate, potassium carbonate, potassium tert.butoxide or 1-hydroxybenztriazole/triethylamine or in the presence of a tertiary organic base such as triethylamine, N-ethyl-diisopropylamine, N-methyl-morpholine or pyridine, which may simultaneously serve as solvent, at temperatures between −30 and 100° C., but preferably at temperatures between −10 and 80° C. However, the reaction may also be carried out with a corresponding acid halide or acid anhydride optionally in the presence of an acid binding agent as described above.

h) In order to prepare compounds of general formula I wherein the group x contains a cyano, alkoxycarbonyl or aralkoxycarbonyl group:

Reacting a compound of general formula

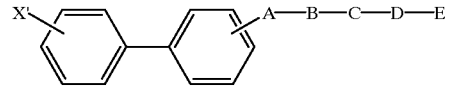
(XII)

wherein

A, B, C, D and E are defined as hereinbefore and X' represents an amino, aminoalkyl, amidino, guanidino or guanidinoalkyl group, with bromocyanogen or with an ester of general formula $Z_3$—CO—$OR_3'$ (XIII)

wherein

R₃' represents an optionally phenyl-substituted C₁₋₃-alkyl group and Z₃ represents a nucleophilic leaving group such as a halogen atom, an azido group, an alkoxycarbonyloxy, aralkoxycarbonyloxy or aryloxy group, e.g. a chlorine or bromine atom or a methoxycarbonyloxy, hoxycarbonyloxy, benzyloxycarbonyloxy or nitrophenyloxy group.

The reaction is conveniently carried out in a solvent such as tetrahydrofuran, chloroform, dimethylformamide, dioxane, methylene chloride or diethylether, optionally in the presence of a base such as sodium carbonate, potassium carbonate, potassium tert.butoxide or 1-hydroxy-benzotriazole/triethylamine or in the presence of a tertiary organic base such as triethylamine, N-ethyl-diisopropylamine, N-methylmorpholine, 4-dimethylaminopyridine or pyridine, which may simultaneously serve as solvent, at temperatures between −30 and 100° C., but preferably at temperatures between −10 and 80° C.

i) In order to prepare compounds of general formula I wherein A or C represents a sulphinyl or sulphonyl group or R₁ or R₂ represents an alkylsulphinyl or alkylsulphonyl group or E contains a 1-oxidothiomorpholino or 1,1-dioxidothiomorpholino group:

Oxidizing a compound of general formula

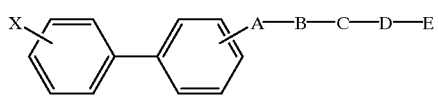

(XIV)

wherein

A, B, C, D, E and X are defined as hereinbefore with the proviso that A or C represents a sulphur atom or a sulphinyl group or R₁ or R₂ contains a sulphenyl or sulphinyl group or E contains a thiomorpholino or 1-oxidothiomorpholino group.

The oxidation is preferably carried out in a solvent or mixture of solvents, e.g. in water, water/pyridine, acetone, glacial acetic acid, methylene chloride, glacial acetic acid/acetanhydride, dilute sulphuric acid or trifluoroacetic acid, at temperatures between −80 and 100° C., depending on the oxidizing agent used.

In order to prepare a corresponding S-oxide compound of general formula I oxidation is appropriately carried out with one equivalent of the oxidizing agent used, e.g. with hydrogen peroxide in glacial acetic acid, trifluoroacetic acid or formic acid at 0 to 20° C. or in acetone at 0 to 60° C., with a peracid such as performic acid in glacial acetic acid or trifluoroacetic acid at 0 to 50° C. or with m-chloroperbenzoic acid in methylene chloride or chloroform at −20 to 60° C., with sodium metaperiodate in aqueous methanol or ethanol at −15 to 25° C., with bromine in glacial acetic acid or aqueous acetic acid, with N-bromo-succinimide in ethanol, with tert.butyl-hypochlorite in methanol at −80 to −30° C., with iodobenzodichloride in aqueous pyridine at 0 to 50° C., with nitric acid in glacial acetic acid at 0 to 20° C., with chromic acid in glacial acetic acid or in acetone at 0 to 20° C. and with sulphurylchloride in methylene chloride at −70° C. and the resulting thioether-chlorine complex is conveniently hydrolysed with aqueous ethanol.

In order to prepare an S,S-dioxide compound of general formula I, oxidation is expediently carried out with one or with two or more equivalents of the oxidizing agent used, e.g. with hydrogen peroxide in glacial acetic acid/acetanhydride, trifluoroacetic acid or in formic acid at 20 to 100° C. or in acetone at 0 to 60° C., with a peracid such as performic acid or m-chloroperbenzoic acid in glacial acetic acid, trifluoroacetic acid, methylene chloride or chloroform at temperatures between 0 and 60° C., with nitric acid in glacial acetic acid at 0 to 20° C., with chromic acid or potassium permanganate in glacial acetic acid, water/sulphuric acid or in acetone at 0 to 20° C.

In reactions a) to i) described hereinbefore, any reactive groups present such as hydroxy, carboxy, amino or alkylamino groups may be protected during the reaction by means of conventional protecting groups which are cleaved again after the reaction.

For example, the protective group for a hydroxy group may be a trimethylsilyl, acetyl, benzoyl, tert.butyl, trityl, benzyl or tetrahydropyranyl group, the protecting group for a carboxyl group may be a trimethylsilyl, methyl, ethyl, tert.butyl, benzyl or tetrahydropyranyl group and the protecting group for an amino, alkylamino or imino group may be an acetyl, benzoyl, ethoxycarbonyl, tert.-butoxycarbonyl, benzyloxycarbonyl, benzyl, methoxybenzyl or 2,4-dimethoxybenzyl group and for the amino group a phthalyl group may also be considered.

The optional subsequent cleaving of a protecting group may, for example, be carried out hydrolytically in an aqueous solvent, e.g. in water, isopropanol/water, tetrahydrofuran/water or dioxane/water, in the presence of an acid such as trifluoroacetic acid, hydrochloric or sulphuric acid or in the presence of an alkali metal base such as sodium hydroxide or potassium hydroxide or by ether cleaving, e.g. in the presence of iodotrimethylsilane, at temperatures between 0 and 100° C., preferably at temperatures between 10 and 50° C.

However, a benzyl, methoxybenzyl or benzyloxycarbonyl group may be cleaved hydrogenolytically, for example, using hydrogen in the presence of a catalyst such as palladium/charcoal in a solvent such as methanol, ethanol, ethyl acetate or glacial acetic acid, optionally with the addition of an acid such as hydrochloric acid at temperatures between 0 and 50° C., but preferably at ambient temperature, under a hydrogen pressure of 1 to 7 bar, preferably 3 to 5 bar.

A methoxybenzyl group may also be cleaved in the presence of an oxidizing agent such as cerium(IV)-ammonium nitrite in a solvent such as methylene chloride, acetonitrile or acetonitrile/water at temperatures between 0 and 50° C., but preferably at ambient temperature.

However, a 2,4-dimethoxybenzyl group is preferably cleaved in trifluoroacetic acid in the presence of anisole.

A tert butyl or tert.butyloxycorbogyl group is preferably cleaved by treating with an acid such as trifluoroacetic or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Furthermore, the compounds of general formula I obtained may be resolved into their enantiomers and/or diastereomers as mentioned hereinbefore. Thus, for example, cis/trans mixtures may be resolved into their cis and trans isomers, and compounds having at least one optically active carbon atom may be resolved into their enantiomers.

Thus, for example, the cis/trans mixtures obtained may be resolved by chromatography into the cis and trans isomers thereof and the compounds of general formula I which occur in racemate form may be separated by methods known per se (cf. Allinger N. L. and Eliel E. L. in "Topics in Stereochemistry", Vol. 6, Wiley Interscience, 1971) into their optical antipodes and compounds of general formula I having at least 2 asymmetric carbon atoms may be separated on the basis of their physical-chemical differences using known methods, e.g. by chromatography and/or fractional crystallization, into the diastereomers thereof which, if they occur in racemic form, may subsequently be separated into the enantiomers as mentioned above.

The separation of enantiomers is preferably effected by column separation on chiral phases or by recrystallisation from an optically active solvent or by reacting with an optically active substance which forms salts or derivatives such as esters or amines with the racemic compound, especially acids and the activated derivatives or alcohols thereof, and separation of the diastereomeric salt mixture or derivative thus obtained, e.g. on the basis of their different solubilities, whilst the free anti-podes may be released from the pure diastereomeric salts or derivatives by the action of suitable agents. Particularly common, optically active acids include, for example, the D- and L-forms of tartaric and dibenzoyltartaric acid, di-o-tolyl tartaric acid, malic, mandelic, camphorsulphonic, glutamic, aspartic or quinic acid. The optically active alcohol may be (+)- or (−)-menthol, for example, and the optically active acyl group in amides may be, for example, (+)- or (−)-menthyloxycarbonyl.

Moreover, the compounds of formula I obtained may be converted into the salts thereof, particularly for pharmaceutical use the physiologically acceptable salts thereof with inorganic or organic acids. Examples of suitable acids include hydrochloric, hydrobromic, sulphuric, phosphoric, fumaric, succinic, lactic, citric, tartaric or maleic acid.

In addition, the new compounds of formula I thus obtained, if they contain a carboxyl group, may subsequently, if desired, be converted into the addition salts thereof with inorganic or organic bases, more particularly, for pharmaceutical use, into the physiologically acceptable addition salts thereof. Examples of suitable bases include sodium hydroxide, potassium hydroxide, cyclohexylamine, ethanolamine, diethanolamine and triethanolamine.

The compounds of formulae II to XIV used as starting materials are known from the literature in some cases or may be obtained by methods known from the literature (see Examples). Moreover, some of them are described in German Patent Application P 40 35 961.1 filed on 2 November 1990, which corresponds to U.S. Pat. No. 5,591,769.

As already mentioned, the new biphenyl derivatives of general formula I and the addition salts thereof, particularly the physiologically acceptable addition salts thereof with inorganic or organic acids or bases, have valuable properties. Thus, the new compounds of general formula I wherein X contains an optionally substitute amino, amidino or guanidino group or a group which may optionally be converted in vivo into an optionally substituted amino, amidino or guanidino group, e.g. an amino, amidino or guanidino group substituted by an alkoxycarbonyl group, and —C—D—E contains carboxyl, sulpho, phosphono, O-alkyl-phosphono or 5-tetrazolyl groups or groups which can be converted in vivo into carboxyl, sulpho, phosphono, 0-alkyl-phosphono or tetrazolyl groups, e.g. alkoxy-substituted carbonyl groups, have valuable pharmacological properties; in addition to having an inhibitory effect on inflammation and bone degradation, they have, in particular, antithrombotic, anti-aggregatory and tumor- or metastasis-inhibiting effects.

The compounds of general formula I wherein X represents a cyano group are valuable intermediate products for preparing the corresponding aminomethyl and amidino compounds of general formula I.

By way of example, the compounds of general formula I were investigated for their biological effects as follows:

Fibrinogen binding to human thrombocytes

The blood obtained by puncturing an antecubital vein is anticoagulated with trisodium citrate (final concentration: 13 mM) and centrifuged for 10 minutes at 170×g. The supernatant platelet-rich plasma is poured onto a Sepharose 2B column (Pharmacia) and eluted with a solution of 90 mM common salt, 14 mM trisodium citrate, 5 mM glucose and 50 mM Tris(hydroxymethyl)aminomethane, adjusted to pH 7.4. The gel-filtered platelets (GFP) appearing before the plasma proteins are used for the binding experiments.

50 $\mu$l of a 60 mM calcium chloride solution, 50 $\mu$l of a 0.6 mM adenosine diphosphate solution, 100 $\mu$l of substance solution or solvent and 50 $\mu$l of fibrinogen solution (containing 3 $\mu$g of $^{125}$I fibrinogen) are added to 750 $\mu$l of GFP and incubated for 20 minutes at ambient temperature. The non-specific binding is determined in the presence of 3 mg/ml of cold fibrinogen.

900 $\mu$l of the incubated material are carefully pipetted onto 250 $\mu$l of silicon oil (AP 38: AR 20, 1:2 V/v, Wacker Chemie) in Eppendorf tubes and centrifuged for 2 minutes at 10,000×g. The aqueous supernatant and some of the oil are drawn off, the tins of the tubes are cut off together with the platelet pellet and the quantity of bound fibrinogen is determined in a gamma counter. The concentration of substance which brings about a 50% inhibition in fibrinogen binding is determined from a series of concentrations and is given as the $IC_{50}$ value.

2. Antithrombotic activity

Method: Thrombocyte aggregation is measured in platelet rich plasma from healthy test subjects using the Born and Cross method (J. Physiol. 170, 397 (1964)). In order to inhibit coagulation the blood is mixed with sodium citrate 3.14% in a ratio by volume of 1:10.

Collagen-induced aggregation: The course of the decrease in optical density of the platelet suspension is photometrically measured and recorded after the addition of the substance which triggers aggregation. The rate of aggregation is deduced from the gradient angle of the density curve. The point on the curve where there is maximum transmittance is used to calculate the optical density.

The quantity of collagen used is as little as possible but sufficient to give an irreversible reaction curve. Standard commercial collagen produced by Hormonchemie of Munich is used. Before the addition of the collagen the plasma is incubated for 10 minutes at 37° C. with the substance. From the measurements obtained, an $EC_{50}$ is determined graphically, relating to a 50% change in optical density in terms of the inhibition of aggregation.

The Table which follows contains the results found:

| Substance (Example No.) | Fibrinogen binding test $IC_{50}$[nM] | Inhibition of platelet aggregation $EC_{50}$[nM] |
|---|---|---|
| 1 | 290 | 1,100 |
| 1 (1) | 160 | 1,100 |
| 1 (2) | 120 | 7,000 |
| 1 (3) | 1,800 | 13,000 |
| 1 (4) | 350 | 1,700 |
| 1 (5) | 65,000 | >100,000 |
| 1 (6) | 330 | 1,200 |
| 1 (7) | 1,900 | 3,800 |

-continued

| Substance (Example No.) | Fibrinogen binding test IC$_{50}$[nM] | Inhibition of platelet aggregation EC$_{50}$[nM] |
| --- | --- | --- |
| 1 (39) | 24 | 100 |
| 1 (41) | 520 | 2,600 |
| 1 (45) | 220 | 2,000 |
| 1 (47) | 470 | 2,700 |
| 1 (65) | 220 | 2,400 |
| 1 (67) | 180 | 350 |
| 1 (68) | 560 | 3,400 |
| 1 (69) | 3,100 | 12,000 |
| 1 (74) | 2,700 | 10,700 |
| 1 (80) | 31 | 40 |
| 1 (94) | | 40 |

Moreover, the compound of Example 8(5) inhibits the collagen-induced thrombocyte aggregation ex vivo in Rhesus monkeys, for example, after oral administration of 1 mg/kg for longer than 8 hours.

The new compounds are well tolerated because after intravenous administration of 60 mg/kg of the compound of Example 1(39), for example, in mice, none of the three animals tested died. Similar results were obtained with the compounds of Example 1, 1(1) and 2(11) at a dosage of 30 mg/kg, whilst during the injection phase with compounds of Examples 1(1) and 2(11) 1 or 2 animals were sedated. Moreover, when 2.0 g/kg of the compound of Example 8(5) was administered by peroral route no toxic effects were observed either in the rat or in the mouse.

In the light of their inhibitory effect on cell-to-cell or cell-to-matrix interactions, the new cyclic imino derivatives of general formula I and the physiologically acceptable addition salts thereof are suitable for combating or preventing diseases in which smaller or greater cell aggregates occur or in which cell-to-matrix interactions play a part, e.g. in treating or preventing venous and arterial thrombosis, cerebrovascular diseases, lung embolism, cardiac infarction, arteriosclerosis, osteoporosis and the metastasis of tumors. They are also suitable for parallel therapy in thrombolysis with fibrinolytics or vascular interventions such as transluminal angioplasty or in the treatment of shock, diabetes and inflammation.

For treating or preventing the diseases mentioned above the dosage is between 0.1 µg and 20 mg/kg body weight, preferably 1 µg to 10 mg/kg body weight, given in up to four doses per day. For this purpose the compounds of formula I produced according to the invention, optionally in conjunction with other active substances, may be incorporated together with one or more inert conventional carriers and/or diluents, e.g. corn starch, lactose, glucose, microcrystalline cellulose, magnesium stearate, polyvinylpyrrolidone, citric acid, tartaric acid, water, water/ethanol, water/glycerol, water/sorbitol, water/polyethylene-glycol, propyleneglycol, stearylalcohol, carboxymethyl-cellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:

EXAMPLE I

4'-Cyano-biphenylyl-4-acetic acid

A mixture of 11.3 g of 4'-bromo-biphenylyl-4-acetic acid (Melting point: 172–175° C., prepared by reacting 4 acetyl-4'-bromo-biphenyl with morpholine and sulphur and subsequent hydrolysis with potassium hydroxide), 3.48 g of copper(I)-cyanide and 100 ml of dimethylformamide is refluxed for 12 hours, cooled and concentrated by evaporation. The residue is distributed between 1N sodium hydroxide solution and methylene chloride to which a little methanol has been added. The aqueous phase is acidified and extracted with methylene chloride. The methylene chloride phase is treated with activated charcoal, evaporated down, the solid residue is triturated with a mixture of ether and petroleum ether and filtered off.

Yield: 5.1 g (55% of theory),

R$_f$ value: 0.46 (silica gel; methylene chloride/ethanol=9:1)

The following compound is obtained analogously:
(1) Methyl 4-cyano-biphenylyl-4'-carboxylate Melting point: 140–142° C.

(The starting methyl-4-bromo-4'-biphenylyl carboxylate (

Melting point: 140–142° C.) is prepared by esterification of 4-bromo-4'-biphenyl-carboxylic acid with methanolic hydrochloric acid, whereby 4-bromo-4'-biphenyl-carboxylic acid is prepared by reacting 4-acetyl-4'-bromo-biphenyl with bromine and sodium hydroxide solution).

EXAMPLE II

4-Cyano-4'-(2-hydroxyethyl)-biphenyl 20.5 g of methyl 4'-cyano-biphenylyl-4-acetate are dissolved in 350 ml of tetrahydrofuran. 1.8 g of lithium borohydride are added with stirring and the mixture is stirred for two days at ambient temperature. The solvent is distilled off, water is added and the precipitate formed is filtered off. It is washed until neutral and used without any further purification.

Yield: 17.2 g (94% of theory)

R$_f$ value: 0.38 (silica gel; methylene chloride)

The following compound is obtained analogously:
(1) 4-Cyano-4'-hydroxymethyl-biphenyl

EXAMPLE III 4-(2-Bromo-ethyl)-4'-cyano-biphenyl

A mixture of 17.2 g of 4-cyano-4'-(2-hydroxyethyl)-biphenyl, 6.8 ml of pyridine and 75 ml of methylene chloride is cooled to −5° C. and 7.8 ml of thionylbromide are added dropwise thereto with stirring. The mixture is allowed to come to ambient temperature, then after 2 hours it is heated to 45° C. for one hour and left to stand overnight at ambient temperature. The methylene chloride phase is washed with ice water until the strongly acidic reaction dies away, then filtered and evaporated down. The residue is used without any further purification.

Yield: 20.4 g (93% of theory)

R$_f$ value: 0.60 (silica gel; methylene chloride)

The following compound is obtained analogously:
(1) 4-Bromomethyl-4'-cyano-biphenyl

EXAMPLE IV

2-[(2-Ethoxycarbonyl-ethyl)-aminosulphonyloxy]-phenol 1.54 g of β-alanine-ethylester-hydrochloride are mixed with 1.9 g of benzo-dioxathiazole-2,2-dioxide, with the addition of 1.55 g of N-ethyl-diisopropylamine dissolved in 10 ml of dimethylformamide, whilst cooling with ice. The mixture is stirred for 2 hours at ambient temperature, the dimethylformamide is eliminated in vacuo (maximum bath temperature 30° C.) and the residue is purified by chromatography on silica gel (eluant: cyclohexane/ethyl acetate= 8:2).

Yield: 1.4 g (48% of theory), $R_f$ value: 0.31 (silica gel; cyclohexane/ethyl acetate=7:3)

EXAMPLE V

3-Carboxy-4'-cyano-4-hydroxy-biphenyl

A solution of 12 g of 4-cyano-4'-methoxy-biphenyl in 75 ml of methylene chloride is given to a mixture of 25 ml of oxalyl chloride, 50 ml of methylene chloride and 25 g of aluminum chloride after stirring for 30 minutes at –20° C. After stirring for 5 hours at -20° C., the reaction mixture is cooled at first with ice and then allowed to come to ambient temperature within 16 hours. After pouring into ice water and stirring for 30 minutes, the reaction mixture is extracted with ethyl acetate and the organic phase is evaporated until the beginning of the crystallization.

Yield: 10.3 g (75% of theory)

Melting point: 244–246° C.

EXAMPLE VI 4-(Carboxymethyloxy)-4'-cyano-biphenyl 32.9 g of 4-(tert.butyloxycarbonylmethyloxy)-4'-cyano-biphenyl dissolved in 250 ml of methylene chloride is mixed slowly with 137 ml of trifluoroacetic acid. After stirring for 3 hours, the reaction mixture is evaporated to dryness and the solid residue is triturated with water.

Yield 26.3 9 (98% of theory)

Melting point: 202–204° C.

EXAMPLE VII 4-(tert.Butyloxycarbonylmethyloxy)-4'-cyano-biphenyl

Prepared analogously to Example 13 from 4-cyano-4'-hydroxy-biphenyl and tert.butyl bromoacetate.

Melting point: 110–112° C.

EXAMPLE VIII

3-Chlorosulphonyl-4'-cyano-4-methoxy-biphenyl

Prepared by refluxing 6,1 g of sodium 4'-cyano-4-methoxy-3-biphenylyl-sulfonate with 30 ml of phosphorous oxychloride and by subsequent pouring into water.

Yield: 4,7 g (81% of theory)

$R_f$ value: 0.29 (silica gel; cyclohexane/ethyl acetate=2:1)

(The used starting compound is prepared by reacting 4'-cyano-4-methoxy-biphenyl with chloro sulfonic acid) Preparation of the final compounds:

EXAMPLE 1

4-Amidino-4'-[[(2-carboxyethyl)aminocarbonyl]methyl]-biphenyl 0.5 g of 4-amidino-4'-[[(2-methoxycarbonylethyl)-aminocarbonyl]methyl]biphenyl are stirred with 10 ml of 1N sodium hydroxide solution for 16 hours at ambient temperature. 0.7 g of ammonium chloride are added, the mixture is evaporated down and the residue is stirred with water. The crystals formed are suction filtered and washed with acetone.

Yield: 0.41 g (97% of theory),

Melting point: above 250° C.

$R_f$ value: 0.04 (silica gel; methylene chloride/ethanol/concentrated ammonia=4:1:0.25)

The following compounds are obtained analogously:

(1) 4-amidino-4'-(4-carboxybutyrylamino)biphenyl (For saponification a mixture of equal parts of 1N sodium hydroxide solution and methanol is used)

Melting point: above 240° C.

$R_f$ value: 0.50 (silica gel; butanol/glacial acetic acid/water=3:1:1)

(2) 4-amidino-4'-[(3-carboxypropyl)aminocarbonyl]-biphenyl

Melting point: above 260° C.

(Lithium hydroxide is used for saponification)

$R_f$ value: 0.06 (silica gel; methylene chloride/ethanol/concentrated ammonia=4:1:0.25)

(3) 4-amidino-4'-[[(carboxymethylamino)carbonyl]-methoxy]-biphenyl

Melting point: 285° C. (decomp.)

Calculated: (x0.5 H$_2$O): C 60.71 H 5.39 N 12.49

Found: 60.36 5.27 12.01

(4) 4-amidino-4'-[[(2-carboxyethyl)aminocarbonyl]-methyloxy]biphenyl

Melting point: 290° C. (decomp.)

Calculated: (x0.75 H$_2$O): C 60.91 H 5.78 N 11.84

Found: 61.38 5.88 11.55

(5) 4-amidino-4'-[[(3-carboxymethylphenyl)-aminocarbonyl]methyl]biphenyl (Lithium hydroxide is used for saponification)

Melting point: 262–264° C.

(6) 4-amidino-4'-[[(4-carboxypiperidino)carbonyl]-methyloxy biphenyl

Melting point: above 250° C.

$R_f$ value: 0.62 (Reversed Phase Ready-made Plate RP8 (E. Merck); methanol/5% sodium chloride solution=6:4)

(7) 4-amidino-4'[[(3-carboxypiperidino, carbonyl]-methyloxy]biphenyl

Melting point: above 250° C.

$R_f$ value: 0.55 (Reversed Phase Ready-made Plate RP8 (E. Merck); methanol/5% sodium chloride solution=6:4)

(8) 4-amidino-4'-[N-(4-carboxybutyryl)-N-methylamino]-biphenyl (9) 4-amidino-4'-[N-(3-carboxypropionyl)-N-methyl-amino]biphenyl

(10) 4-amidino-4'-[(2-carboxyethyl)aminocarbonyl]-biphenyl

(11) 4-aminomethyl-4'-[N-(4-carboxybutyryl)-N-methyl-amino]biphenyl

(12) 3-(5-carboxyvalerylamino)-3'-guanidinobiphenyl

(13) 4-amidino-4'-[N-[(carboxymethylamino)-carbonylmethyl]-N-methylamino]biphenyl

(14) 4-amidino-3'-bromo-4'-(4-carboxybutyrylamino)-biphenyl

(15) 4-amidino-4'-(4-carboxybutyrylamino)-3',5'-dibromobiphenyl

(16) 4-amidino-4'-[2-(carboxymethylthio)ethyl]biphenyl

(17) 4-amidino-4'-[(3-carboxypropylthio)methyl]biphenyl

(18) 4-amidino-4'-[(carboxymethyloxy) methylcarbonylamino]biphenyl

(19) 4-amidino-4'-[(N-carboxymethyl-N-methylamino)-methylcarbonylamino]biphenyl

(20) 4-amidino-4'-[(2-carboxyethylthio)methylcarbonyl]-biphenyl

(21) 4-amidino-4'-(5-carboxypentyloxy)-3'-methoxybiphenyl

(22) 4-amidino-4'-[(N-(3-carboxy-2-propenyl)-N-methylamino]carbonyl]biphenyl
(23) 4-(5-carboxypentyloxy)-4'-(N-methylamidino)-biphenyl
(24) 4-(5-carboxypentyloxy)-4'-(N-methoxyamidino)-biphenyl
(25) 4-(5-carboxypentyloxy)-4'-hydrazidinobiphenyl
(26) 4-[(3-carboxypropyl)aminocarbonyl]-4'-(N-ethoxycarbonylamidino)biphenyl
(27) 4-(N-benzyloxycarbonylamidino)-4'-[(3-carboxypropyl)aminocarbonyl]biphenyl
(28) 4-amidino-4'-[[[N-(2-carboxyethyl)-N-methylamino]-carbonyl]methyloxy)biphenyl
(29) 4-[2-[N-acetyl-N-(2-carboxyethyl)amino]ethyloxy]-4'-amidinobiphenyl
(30) 4-amidino-4'-[2-[N-(2-carboxyethyl)-N-methanesulphonylamino]ethyloxy]biphenyl
(31) 4-amidino-4'-[2-[N-benzoyl-N-(2-carboxyethyl)-amino]ethyloxy]biphenyl
(32) 4-amidino-4'-[(3-carboxypropylamino)sulphonyl]-biphenyl
(33) 4-amidino-4'-[[N-(3-carboxypropyl)-N-methylamino]-sulphonyl]biphenyl
(34) 4-amidino-4'-[(2-carboxyethyleamino) carbonylamnino]-biphenyl
(35) 4-amiidino-4'-[N-[[N-(2-carboxyethyl)-N-methylamino]carbonyl)]-N-methylamino]biphenyl
(36) 4-amidino-4'-[(3-carboxymethylphenyl)-aminocarbonyl]biphenyl
(Lithium hydroxide is used for saponification)
Melting point: above 260° C.
(37) 4-amidino-4'-[[3-(2-carboxyethyl)phenyl]-aminocarbonyl]biphenyl
(Lithium hydroxide is used for saponification)
Melting point: above 260° C.
(38) 4-amidino-4'-[[3-(2-carboxyethyl)phenyl]-aminocarbonylmethyl]biphenyl
(Lithium hydroxide is used for saponification)
Melting point: 262–264° C.
(39) 4-amidino-4'-[(4-carboxymethylpiperidino)-carbonyl] biphenyl hydrochloride
(Lithium hydroxide is used for saponification)
Melting point: 241–245° C. (decomp.)
(40) 4-amidino-4'-[(4-carboxymethylpiperidino)methyl]-biphenyl
Melting point: 318–320° C. (decomp.)
(41) 4-amidino-4'-[(3-carboxymethylpiperidino)-carbonyl] biphenyl hydrochloride
(Lithium hydroxide is used for saponification)
Melting point: 240–244° C. (decomp.)
(42) 4-amidino-4'-(3-carboxymethylpiperidino)methyl]-biphenyl
(43) 4-amidino-4'-[(3-carboxymethylpyrrolidino)-carbonyl] biphenyl
(44) 4-amidino-4'-[(3-carboxymethylpyrrolidino)-methyl] biphenyl
(45) 4-amidino-4'-[(4-carboxypiperidino)-carbonylmethyl] biphenyl hydrochloride
(Lithium hydroxide is used for saponification)
Melting point: 260–264° C. (decomp.)
(46) 4-amidino-4'-(2-(4-carboxypiperidino)ethyl]-biphenyl
(47) 4-amidino-4'-[(3-carboxymethylpiperidino)-carbonylmethyl]biphenyl hydrochloride
(Lithium hydroxide is used for saponification)
$R_f$ value: 0.16 (silica gel; methylene chloride/ethanol= 4:1)
(48) 4-amidino-4'-[2-(3-carboxymethylpiperidino)-ethyl] biphenyl

(49) 4-amidino-4'-[(3-carboxymethylpyrrolidino)-carbonylmethyl]biphenyl
(50) 4-amidino-4'-[2-(3-carboxymethylpyrrolidino)-ethyl] biphenyl
(51) 4-amidino-4'-[(3-carboxypiperidino)-carbonylmethyl] biphenyl
(52) 4-amidino-4'-[2-(3-carboxypiperidino)ethyl]-biphenyl
(53) 4-amidino-4'-(5-carboxypentyloxy)-3'-methane-sulphonylaminobiphenyl
(54) 4-amidino-3'-benzenesulphonylamino-4'-(5-carboxy-pentyloxy)biphenyl
(55) 4-amidino-4'-(4-carboxybutylthio)-biphenyl
(56) 4-amidino-4'-[(4-carboxybutyl)sulphinyl]biphenyl
(57) 4-amidino-4'-[(4-carboxybutyl)sulphonyl]biphenyl
(58) 4-amidino-4'-[(3-carboxypropyl)sulphinylmethyl]-biphenyl
(59) 4-amidino-4'-[(3-carboxypropyl)sulphonylmethyl]-biphenyl
(60) 4-amidino-4'-(5-carboxypentyloxy)-3'-hydroxybiphenyl
(61) 4-amidino-4'-(5-carboxypentyloxy)-3'-methylthiobiphenyl
(62) 4-amidino-4'-(5-carboxypentyloxy)-3'-methylsulphinylbiphenyl
(63) 4-amidino-4'-(5-carboxypentyloxy)-3'-methylsulphonylbiphenyl
(64) 4-amidino-4'-[(4-carboxymethylpiperidino)-carbonylmethyl]biphenyl hydrochloride
(Lithium hydroxide is used for saponification)
(65) 4-amidino-4'-[(4-carboxybutyl)aminocarbonyl]-biphenyl hydrochloride
(Lithium hydroxide is used for saponification)
Melting point: 275–278° C. (decomp.)
(66) 4-amidino-4'-(4-carboxybutyloxy)biphenyl
Melting point: above 300° C.
Calculated: (×0.1 $H_2O$): C 68.80 H 6.45 N 8.92
Found: 68.80 6.47 8.52
(67) 4-amidino-4'-[(4-carboxymethytpiperazino)-carbonyl] biphenyl hydrochloride
(Lithium hydroxide is used for saponification)
Melting point: above 300° C.
Calc. ×1 HCl: C 59.62 H 5.75 Cl 8.80 N 13.91
Found: 59.09 5.80 9.15 13.30
(68) 4-amidino-4'-[[4-(2-carboxyethyl)piperazino)-carbonyl]biphenyl dihydrochloride
(Lithium hydroxide is used for saponification)
Melting point:. 282–286° C. (decomp.)
(69) 4-amidino-4'-[(2-carboxyethyl)aminosulphonyl-amino] biphenyl
(Lithium hydroxide is used for saponification)
Melting point: above 265° C.
$R_f$ value: 0.84 (Reversed Phase Ready-made Plate RP8 (E. Merck); methanol/10% sodium chloride solution= 60:40)
(70) 4-butylamidino-4'-[(4-carboxymethylpiperidino)-carbonyl]biphenyl
(71) 4-[(4-carboxymethylpiperidino)carbonyl]-4'-methylamidinobiphenyl
(72) 4-amidino-4'-[(4-carboxymethylenepiperidino)-carbonyl]biphenyl
Melting point: 317–319° C. (decomp.)
(73) 4-amidino-4'-(4-carboxymethyloxyphenyl)biphenyl
(74) 4-amidino-4'-[(4-carboxypiperidino)carbonyl)-biphenyl hydrochloride
(Lithium hydroxide is used for saponification)
Melting point: 303–308° C. (decomp.)
(75) 4-aminomethyl-4'-[[(4-carboxypiperidino)carbonyl]-methyl]biphenyl

21

(76) 4-aminomethyl-4'-[(4-carboxymethylpiperidino)-methyl]biphenyl
(77) 4-amidino-4'-[(4,4-bis-carboxymethylpiperidino)-carbonyl]biphenyl
(78) 4-aminomethyl-4'-[(4-carboxymethylenepiperidino)-carbonyl]biphenyl
(79) 4-aminomethyl-4'-[(4,4-bis-carboxymethyl-piperidino)carbonyl]biphenyl
(80) 4-amidino-4'-[(4-carboxycyclohexyl)aminocarbonyl]-biphenyl hydrochloride
Melting point: 344–348° C. (decomp.)
(81) 4-aminomethyl3'-[(4-carboxybutyl)aminosulphonyl]-4'-methoxybiphenyl
Melting point: 268–270° C. (sinters from 190° C.)
$R_f$ value: 0.14 (silica gel; methylene chloride/methanol/concentrated ammonia=4:1:0.25)
(82) 4-amidino-3'-[(4-carboxybutyl)aminosulphonyl]-4'-methoxybiphenyl
$R_f$ value: 0.13 (silica gel; methylene chloride/methanol/concentrated ammonia=2:1:0.25)
(83) 4-aminomethyl-3'-[(4-carboxybutyl)aminocarbonyl]-4'-methoxybiphenyl
(84) 4-amidino-3'-[(4-carboxybutyl)aminocarbonyl]-4'-methoxybiphenyl
(85) 4-amidino-4'-(2-carboxyethyloxy)biphenyl
(86) 4-amidino-4'-(carboxymethyloxy)biphenyl
(87) 4-amidino-4'-[(3,3-bis-carboxymethylpropyl)-aminocarbonyl]biphenyl
(88) 4-amidino-4'-[[N-(3,3-bis-carboxyinethylpropyl)-N-methyl]aminocarbonyl]biphenyl
(89) 4-amidino-3'-[(4-carboxycyclohexyl)aminocarbonyl]-4'-methoxybiphenyl
$R_f$ value: 0.40 (silica gel; methylene chloride/methanol= 2:1)
(90) 4-amidino-3'-[(4-carboxycyclohexyl)aminocarbonyl]-4'-hydroxybiphenyl
(91) 4-amidino-3'-[N-(4-carboxycyclohexyl)-N-methyl-aminocarbonyl]-4'-methoxybiphenyl
(92) 4-amidino-3'-[(4-carboxycyclohexyl)-aminosulphonyl]-4'-methoxybiphenyl
(93) 4-aminomethyl-3'-[(4-carboxycyclohexyl)-aminocarbonyl]biphenyl
(94) 4-amidino-4'-[N-(4-carboxycyclohexyl)-N-methyl-aminocarbonyl]biphenyl
Melting point:
(95) 4-amidino-4'-[N-(3-carboxypropyl)-N-methyl-aminocarbonyl]biphenyl
Melting point: 282–285° C. (decomp.)
(96) 4-aminomethyl-3'-[N-(4-carboxy-cyclohexyl)-N-methyl-aminocarbonyl]-4'-hydroxy-biphenyl (Lithium hydroxide is used for saponification)
Melting point: 245–250° C. (decomp.)
$R_f$ value: 0.05 (silica gel; methylene chloride/methanol/concentrated ammonia=2:1:0.5)
(97) 4-aminomethyl-3'-[(4-carboxy-cyclohexyl)-aminocarbonyl]-4'-methoxy-biphenyl
(98) 4-amidio-3'-(N-(4-carboxy-cyclohexyl)-N-methylaminocarbonyl]-4'-hydroxy-biphenyl
Melting point: from 290° C. (decomp.)
$R_f$ value: 0.34 (silica gel; roethylene chloride/methanol= 2:1)

EXAMPLE 2

4-Amidino-4'-(5-carboxypentyloxy)biphenyl hydrochloride 0.5 g of di[4-amidino-4'-(5-methoxycarbonylpentyloxy) biphenyl] dihydrogencarbonate are stirred in 15 ml of 8N hydrochloric acid for 5 weeks at ambient temperature and 5 days at 40° C. The mixture is diluted with water, filtered and the residue is washed with water and acetone.

Yield: 0.43 g (92% of theory),
Melting point: above 250° C.
Calculated (×0.6 HCl): C 65.53 H 6.54 N 8.04 Cl 6.11
Found: 65.30 6.51 7.55 6.31

The following compounds are obtained analogously:
(1) 4-amidino-4'-(3-carboxypropyloxy)biphenyl
Melting point: above 290° C
Calculated (×0.75 HCl×0.25 H$_2$O) C 61.84 H 5.88 N 8.48 Cl 8.05
Found: 61.85 5.90 8.46 8.27
(2) 4-amidino-4'-(4-carboxybutyloxy)biphenyl
(3) 4-amidino-4'-(5-carboxypentyloxy)-3'-nitro-biphenyl
(4) 4-amidino-3'-amino-4'-(5-carboxypentyloxy)biphenyl
(5) 3-acetylamino-4'-amidino-4-(5-carboxypehtyloxy)-biphenyl
(6) 4-amidino-3'-benzoylamino-4'-(5-carboxypentyloxy)-biphenyl
(7) 4-amidino-4'-(5-carboxypentyloxy)-3-chlorobiphenyl
(8) 4-amidino-4'-(5-carboxypentyloxy)-3-fluorobiphenyl
(9) 4-amidino-4'-(5-carboxypentyloxy)-2',3'-dimethyl-biphenyl
(10) 4-amidino-4'-(5-carboxypentyloxy)-3'-trifluoromethylbiphenyl
(11) 4-amidino-4'-[[2-carboxy-1-[[2-(4-methoxyphenyl)-ethyl]aminocarbonyl]ethylamino]carbonylmethyl] biphenyl hydrochloride
(One works in a 1:1- mixture of 2N hydrochloric acid and tetrahydrofuran; reaction lasts 72 hours)
$R_f$ value: 0.50 (Reversed Phase Ready-made Plate RP18 (E. Merck); acetonitrile/water/acetic acid=5:5:0.1).

EXAMPLE 3

4-Amidino-4'-[[[2-carboxy-1-[[2-(4-methoxyphenyl)-ethyl]aminocarbonyl]ethylamino] carbonylmethyl]-aminocarbonyl]biphenyl hydrochloride 0.67 g of 4-(N-benzyloxycarbonylamidino)-4'-[[[2-benzyloxycarbonyl-1-[[2-(4-methoxyphenyl)ethyl]-aminocarbonyl]ethylamino]carbonylmethyl] aminocarbonyl]-biphenyl are hydrogenated in 100 ml of methanol with hydrogen under 5 bars of pressure in the presence of 0.2 g of 5% palladium charcoal at ambient temperature for 2 hours. The catalyst is filtered off, the filtrate is washed with methanol and a little 1N hydrochloric acid and evaporated down. The residue is triturated with ether and filtered off.

Yield: 0.48 g (92% of theory),
Melting point: 202–205° C. (decomp.)
The following compounds are obtainer analogously:
(1) 4-[(3-carboxypropylamino)carbonyl]-4'-(N-methoxycarbonylamidino)biphenyl
(Dimethylformamide is used as solvent and 10% palladium/charcoal as catalyst)
(2) 4-amidino-4'-[(4-carboxymethyl-4-hydroxy-piperidino) carbonyl]biphenyl
(3) 4-[(4-carboxymethylpiperidino)carbonyl]-4'-(N-methoxycarbonylamidino)biphenyl
One works using 10% palladium/charcoal in dioxane
Melting point: 194–196° C. (decomp.)
$R_f$ value: 0.14 (silica gel; methylene chloride/ethanol= 9:1)

EXAMPLE 4

4-Amidino-4'-[2-[(2-carboxyethyl)carbonylamino]ethyl]-biphenyl 0.27 g of 4-amidino-4'-(2-succinimidoethyl)-biphenyl are dissolved in 10 ml of dimethylsulphoxide, mixed with 0.8 ml of 1N sodium hydroxide solution and stirred for 5 hours at ambient temperature. The precipitate formed is filtered off, washed with dimethylsulphoxide, digested with 0.01N hydrochloric acid, suction filtered and washed with water.

Yield: 0.07 g (25% of theory),

Melting point: above 240° C.

$R_f$ value: 0.51 (silica gel; methylene chloride/methanol= 8:2)

EXAMPLE 5

4-Amidino-4'-[(4-benzyloxycarbonylmethylpiperidino)-carbonyl] biphenyl toluenesulphonate A mixture of 1.6 g of 4-amidino-4'-[(4-carbonylmethylpiperidino)carbonyl)biphenyl hydrochloride, 50 ml of benzyl alcohol and 1 g of p-toluonesulphonic acid is heated to 70° C. with stirring for 4 hours under 100 mbar and then evaporated down in a water jet vacuum at 140–150° C. The residue was triturated with ether, the solid product obtained was filtered off and dissolved in dimethylformamide, the solution was evaporated down and the residue was triturated with ether.

Yield: 2.46 g (98% of theory),

Melting point: 218–223° C. (decomp.)

The following compounds were obtained analogously, in each case working in dimethylformamide with a 12-fold molar excess of the alcohol in question and a 15-fold excess of p-toluenesulphonic acid:

(1) 4-amidino-4'-[[4-(n-butyloxycarbonylmethyl)-piperidino]carbonyl]biphenyl toluenesulphonate (2) 4-amidino-4'-[[4-(2-phenylethyl) oxycarbonylmethylpiperidino]carbonyl]biphenyl toluenesulphonate (3) 4-amidino-4'-[[4-[2-(2-oxopyrrolidinyl)ethyl]-oxycarbonylmethylpiperidino]carbonyl]biphenyl toluenesulphonate (4) 4-amidino-4'-[[4-[(3-pyridyl)methyl] oxycarbonylmethylpiperidino]carbonyl]biphenyl toluenesulphonate (5) 4-amidino-4'-[[4-(2-morpholinoethyl) oxycarbonylmethylpiperidino)carbonyl]biphenyl toluenesulphonate (6) 4-amidino-4'-[[4-(2-thiomorpholinoethyl)-oxycarbonylmethylpiperidino]carbonyl]biphenyl (7) 4-[[4-(n-butyloxycarbonylmethyl)piperidino]-carbonyl]-4'-(N-methylamidino)biphenyl

EXAMPLE 6

Di-[4-Amidino-4'-(5-methoxycarbonylpentyloxy) biphenyl]dihydrogencarbonate 75 ml of methanol are covered with 30 ml of petroleum ether and hydrogen chloride gas is introduced, whilst cooling with ice, until saturation point. Then 2.1 g of 4-cyano-4'-(5-ethoxycarbonylpentyloxy)biphenyl are added and the mixture is stirred for 18 hours at ambient temperature. It is evaporated to dryness in vacuo, the residue is suspended in methanol, 5.36 g of ammonium carbonate are added and the mixture is stirred for 16 hours at ambient temperature. The precipitate obtained is filtered off and purified by stirring with methylene chloride/methanol (85:15) and water.

Yield: 1.75 g (75% of theory),

Melting point: 185–189° C. (decomp.)

Calculated (×0.5 $H_2CO_3$): C 66.31 H 6.74 N 7.55

Found: 66.75 6.85 7.41

The following compounds are obtained analogously:

(1) 4-amidino-4'-(4-methoxycarbonylbutyrylamino)-biphenyl hydrochloride

Melting point: from 210° C. (decomp.)

$R_f$ value: 0.13 (silica gel; ethyl acetate/ethanol=7:3)

(2) 4-amidino-4'-[[(4-methoxycarbonylmethyl)-aminocarbonyl]methyloxy]biphenyl hydrochloride Melting point: 223–225° C. (decomp.)

$R_f$ value: 0.06 (silica gel; methylene chloride/methanol= 10:1)

(3) 4-amidino-4'-[[(2-methoxycarbonylethyl)-aminocarbonyl]methyloxy]biphenyl hydrochloride Melting point: 155° C. (decomp.)

$R_f$ value: 0.18 (silica gel; methylene chloride/methanol= 10:1)

(4) 4-amidino-4'-[[3-(methoxycarboxylmethyl)phenyl]-aminocarbonyl]biphenyl hydrochloride Melting point: over 260° C.

$R_f$ value: 0.27 (silica gel; methylene chloride/ethanol= 4:1)

(5) 4-amidino-4'-((2-methoxycarbonylethyl)-aminocarbonylmethyl]biphenyl

[The product is purified by chromatography on silica gel (eluant: methylene chloride/ethanol/concentrated ammonia= 4:1:0.25)]

$R_f$ value: 0.20 (silica gel; methylene chloride/ethanol/ concentrated ammonia 4:1:0.25)

(6) 4-amidino-4'-[(3-methoxycarbonylpropyl)-aminocarbonyl]biphenyl hydrochloride Melting point: 210–212° C.

$R_f$ value: 0.17 (silica gel; methylene chloride/ethanol/ concentrated ammonia 4:1:0.25)

(7) 4-amidino-4'-[N-(3-methoxycarbonylbutyryl)-N-methylamino]biphenyl hydrochloride (8) 4-amidino-4'-(3-methoxycarbonylpropyloxy)biphenyl dihydrogencarbonate Melting point: 203–205° C.

(9) 4-amidino-4'-(4-methoxycarbonylbutyloxy)biphenyl hydrochloride (A 10:1 mixture of methanol and concentrated aqueous ammonia is used to convert the iminoester obtained as an intermediate product into the amidine)

Melting point: 190–194° C.

(10) 4-amidino-4'-[N-(3-methoxycarbonylpropionyl)-N-methylamino]biphenyl hydrochloride

(11) 4-amidino-4'-[(2-methoxycarbonylethyl)-aminocarbonyl]biphenyl hydrochloride

(12) 4-amidino-4'-[N-[(methoxycarbonylmethyl)-aminocarbonylmethyl]-N-methylamino)biphenyl hydrochloride

(13) 4-amidino-3'-bromo-4'-[(4-methoxycarbonylbutyryl)-amino]biphenyl hydrochloride

(14) 4-amidino-3',5'-dibromo-4'-[(4-methoxycarbonylbutyryl)amino]biphenyl hydrochloride

(15) 4-amidino-4'-(5-methoxycarbonylpentyloxy)-3'-nitro-biphenyl hydrochloride

(16) 4-amidino-3'-amino-4'-(5-methoxycarbonylpentyloxy) biphenyl hydrochloride

(17) 3-acetylamino-4'-amidino-4-(5-methoxycarbonylpentyloxy)biphenyl hydrochloride

(18) 4-amidino-3'-benzoylamino-4'-(5-methoxycarbonylpentyloxy)biphenyl hydrochloride
(19) 4-amidino-3'-methanesulphonylamino-4'-(5-methoxycarbonylpentyloxy)biphenyl hydrochloride
(20) 4-amidino-3'-benzenesulphonylamino-4'-[(5-methoxycarbonylpentyloxy)biphenyl hydrochloride
(21) 4-amidino-4'-(4-methoxycarbonylbutylthio)biphenyl hydrochloride
(22) 4-amidino-4'-[(4-methoxycarbonylbutyl)sulphonyl]-biphenyl hydrochloride
(23) 4-amidino-4'-[2-(methoxycarbonylmethylthio)-ethyl]biphenyl hydrochloride
(24) 4-amidino-4'-[(3-methoxycarbonylpropylthio)-methyl]biphenyl hydrochloride
(25) 4-amidino-4'-[(3-methoxycarbonylpropyl)-sulphonylmethyl]biphenyl hydrochloride
(26) 4-amidino-4'-[[(methoxycarbonylmethyloxy)methyl]-carbonylamino]biphenyl hydrochloride
(27) 4-amidino-4'-[[N-(methoxycarbonylmethyl)-N-methylamino]methyl]carbonylamino]biphenyl hydrochloride
(28) 4-amidino-4'-[(2-methoxycarbonylethylthio)methylcarbonyl]biphenyl hydrochloride
(29) 4-amidino-3'-hydroxy-4'-(5-methoxycarbonylpentyloxy)biphenyl hydrochloride
(30) 4-amidino-3'-methoxy-4'-(5-methoxycarbonylpentyloxy)biphenyl hydrochloride
(31) 4-amidino-3-chloro-4'-(5-methoxycarbonylpentyloxy)biphenyl hydrochloride
(32) 4-amidino-3-fluoro-4'-(5-methoxycarbonylpentyloxy)biphenyl hydrochloride
(33) 4-amidino-2',3'-dimethyl-4'-(5-methoxycarbonylpentyloxy)biphenyl hydrochloride
(34) 4-amidino-4'-(5-methoxycarbonyl-pentyloxy)-3'-trifluoromethylbiphenyl hydrochloride
(35) 4-amidino-4'-([N-(3-methoxycarbonyl-2-propenyl)-N-methylamino)carbonyl)biphenyl hydrochloride
(36) 4-[(5-methoxycarbonylpentyloxy)-4'-(N-methyl-amidino)biphenyl
(The iminoester is taken up in absolute methanol and reacted with a 20-fold excess of a methanolic methylamine solution)
(37) 4-amidino-4'-[[[N-(2-methoxycarbonylethyl)-N-methylamino]carbonyl]methyloxy]biphenyl hydrochloride
(38) 4-[2-[N-acetyl-N-(2-methoxycarbonylethyl)amino]-ethyloxy]-4'-amidinobiphenyl hydrochloride
(39) 4-amidino-4'-(2-(N-methanesulphonyl-N-(2-methoxycarbonylethyl)amino]ethyloxy]biphenyl hydrochloride
(40) 4-amidino-4'-[2-[N-benzoyl-N-(2-methoxycarbonylethyl)amino]ethyloxy]biphenyl hydrochloride
(41) 4-amidino-4'-[(3-methoxycarbonylpropylamino)-sulphonyl]biphenyl hydrochloride
(42) 4-amidino-4'-[[N-(3-methoxycarbonylpropyl)-N-methylamino]sulphonyl]biphenyl hydrochloride
(43) 4-amidino-4'-[(2-methoxycarbonylethyl)-aminocarbonylamino]biphenyl hydrochloride
(44) 4-amidino-4'-[N-[[N-(2-methoxycarbonylethyl)-N-methylamino]carbonyl]-N-methylamino]biphenyl hydrochloride
(45) 4-amidino-4-[[3-(2-methoxycarbonylethyl)phenyl]-aminocarbonyl]biphenyl hydrochloride
Melting point: 266–268° C. (decomp.)
(46) 4-amidino-4'-[[[3-(methoxycarbonylmethyl)phenyl]-aminocarbonyl]methyl]biphenyl hydrochloride
$R_f$ value: 0.48 (silica gel; methylene chloride/ethanol= 4:1)
(47) 4-amidino-4'-[[[(3-(2-methoxycarbonylethyl)phenyl]-aminocarbonyl]methyl]biphenyl hydrochloride
$R_f$ value: 0.38 (silica gel; methylene chloride/ethanol= 4:1)
(48) 4-amidino-4'-[[(4-methoxycarbonylpiperidino)-carbonyl]methyloxy]biphenyl hydrochloride
Melting point: 240° C. (decomp.)
$R_f$ value: 0.33 (silica gel; methylene chloride/ethanol=9:1)
(49) 4-amidino-4'-[[(3-methoxycarbonylpiperidino)-carbonyl]methyloxy]biphenyl hydrochloride
$R_f$ value: 0.78 (silica gel; methylene chloride/ethanol= 8:2)
(50) 4-amidino-4'-[(4-methoxycarbonylmethylpiperidino)-carbonyl]biphenyl hydrochloride
Melting point: 268–270° C.
(51) 4-amidino-4'-[(4-methoxycarbonylmethylpiperidino)-methyl]biphenyl hydrochloride
Melting point: 148–150° C. (decomp.)
(52) 4-amidino-4'-[(3-methoxycarbonylmethylpiperidino)-carbonyl]biphenyl hydrochloride
Melting point: 277–280° C.
(53) 4-amidino-4'-[(3-methoxycarbonylmethylpiperidino)-methyl biphenyl hydrochloride
(54) 4-amidino-4'-[(3-methoxycarbonylmethylpyrrolidino)carbonyl]biphenyl hydrochloride
(55) 4-amidino-4'-[(3-methoxycarbonylmethylpyrrolidino)methyl]biphenyl hydrochloride
(56) 4-amidino-4'-[(4-methoxycarbonylpiperidino)-carbonylmethyl]biphenyl hydrochloride
Melting point: 224–228° C. (decomp.)
(57) 4-amidino-4'-[2-(4-methoxycarbonylpiperidino)-ethyl]biphenyl hydrochloride
(58) 4-amidino-4'-[(3-methoxycarbonylmethylpiperidino)-carbonylmethyl]biphenyl hydrochloride
Melting point: 166–172° C.
(59) 4-amidino-4'-[2-(3-methoxycarbonylmethylpiperidino)ethyl]biphenyl hydrochloride
(60) 4-amidino-4'-[(3-methoxycarbonylmethylpyrrolidino)carbonylmethyl]biphenyl hydrochloride
(61) 4-amidino-4'-[2-(3-methoxycarbonylmethylpyrrolidino)ethyl]biphenyl hydrochloride
(62) 4-amidino-4'-[3-methoxycarbonylpiperidino)-carbonylmethyl]biphenyl hydrochloride
(63) 4-amidino-4'-[2-(3-methoxycarbonylpiperidino)-ethyl]biphenyl hydrochloride
(64) 4-amidino-4-(4-sulphobutyloxy)biphenyl
(65) 4-amidino-4'-(4-phosphonobutyloxy)biphenyl hydrochloride
(66) 4-amidino-4'-[4-(O-methyl-phosphono)butyloxy]-biphenyl hydrochloride
(67) 4-amidino-4'-(5-methoxycarbonylpentyloxy)-3'-methylthiobiphenyl hydrochloride
(68) 4-amidino-4'-(5-methoxycarbonylpentyloxy)-3'-methylsulphonylbiphenyl hydrochloride
(69) 4-amidino-4'-[3-(5-tetrazolyl)propyloxy]biphenyl hydrochloride
(70) 4-amidino-4'-((2-methoxycarbonyl-1-[[2-(4-methoxyphenyl)ethyl]aminocarbonyl]ethylamino]carbonylmethyl]-biphenyl
$R_f$ value: 0.11 (silica gel; methylene chloride/methanol= 9:1)
(71) 4-amidino-4'-[(4-methoxycarbonylmethylpiperidino)-carbonylmethyl)biphenyl hydrochloride Melting point: 172–177° C.
(72) 4-amidino-4'-[(4-methoxycarbonylbutyl) aminocarbonyl]biphenyl hydrochloride
Melting point: 208–212° C.
(73) 4-amidino-4'-[(4-ethoxycarbonylmethylpiperidino)-carbonyl]biphenyl
$R_f$ value: 5 0.19 (silica gel; methylene chloride/ethanol= 4:1)
(74) 4-amidino-4'-((4-methoxycarbonylmethylpiperazino)-carbonyl]biphenyl dihydrochloride
Melting point: 274–276° C.
(75) 4-amidino-4'-[[(4-(2-methoxycarbonylethyl)-piperazino]carbonyl]biphenyl dihydrochloride
Melting point: 292–296° C. (decomp.)
Calculated (×2 HCl×H$_2$O): C 54.53 H 6.23 N 11.54 Cl 14.61
Found: 54.44 5.93 11.50 14.41
(76) 4-amidino-4'-[(2-methoxycarbonylethyl)-aminosulphonylamino]biphenyl hydrochloride
Melting point: sinters above 176° C. (decomp.)
Calculated: C 48.63 H 5.32 N 12.97 S 7.42 Cl 9.03
Found: 48.58 5.27 12.66 7.51 8.81
(77) 4-(n-butyl-amidino)-4'-[(4-methoxycarbonylmethylpiperidino)carbonyl]biphenyl
(n-butylamine is used in the second stage of the reaction).
(78) 4-[(4-methoxycarbonylmethylpiperidino)carbonyl]-4'-(N-methylamidino)biphenyl
(Aqueous methylamine solution is used in the second stage of the reaction).
(79) 4-amidino-4'-[(4-methoxycarbonylmethylenepiperidino)carbonyl]biphenyl
Melting point: 298–300° C. (decomp.)
(80) 4-amidino-4'-(4-methoxycarbonylmethyloxyphenyl)-biphenyl
(81) 4-amidino-4'-[(4-methoxycarbonylpiperidino)-carbonyl]biphenyl
Melting point: 294–296° C. (decomp.)
(82) 4-amidino-4'-[(4-dimethylaminocarbonylmethylpiperidino)carbonyl]biphenyl
(83) 4-amidino-4'-[(4-sulphomethylpiperidino)carbonyl]-biphenyl
Melting point:
(84) 4-amidino- 4'-[(4-(5-tetrazolylmethyl)piperidino]-carbonyl)biphenyl
(85) 4-amidino-4'-[(4,4-bis-methoxycarbonylmethylpiperidino)carbonyl]biphenyl
(86) 4-amidino-4-(aminocarbonylmethylaminocarbonyl)-biphenyl hydrochloride
Prepared from 4-cyano-4'-methoxycarbonylmethylaminocarbonyl)biphenyl
Melting point: above 260° C.
$R_f$ value: 0.28 (silica gel: methylene chloride/ethanol= 4:1)
(87) 4-amidino-4'-[(4-methoxycarbonylcyclohexyl)-aminocarbonyl]biphenyl hydrochloride
Melting point: 302–305° C. (decomp.)
(88) 4-amidino-4'-(2-methoxycarbonylethyloxy)biphenyl
(89) 4-amidino-4'-(methoxycarbonylmethyloxy)biphenyl
(90) 4-amidino-4'-[(3,3-bis-methoxycarbonylmethylpropyl) aminocarbonyl]biphenyl
(91) 4-amidino-4'-(N-(3,3-bis-methoxycarbonylmethylpropyl)-N-methylaminocarbonyl]biphenyl
(92) 4-amidino-4'-methoxy-3'-[(4-methoxycarbonylbutyl)-aminosulphonyl]biphenyl hydrochloride
$R_f$ value: 0.19 (silica gel; methylene chloride/methanol/concentrated ammonia=4:1:0.25)
(93) 4-amidino-4'-methoxy-3'-[(4-methoxycarbonylbutyl)-aminocarbonyl]biphenyl
(94) 4-amidino-4'-methoxy-3'-[(4-methoxycarbonylcyclohexyl)aminocarbonyl]biphenyl
$R_f$ value: 0.15 (silica gel; methylene chloride/methanol= 9:1)
(95) 4-amidino-4'-hydroxy-3'-(4-methoxycarbonylcyclohexyl)aminocarbonyl]biphenyl
(96) 4-amidino-4'-methoxy-3'-[N-(4-methoxycarbonylcyclohexyl)-N-methylaminocarbonyl] biphenyl
Melting point:
(97) 4-amidino-4'-methoxy-3'-[(4-methoxycarbonylcyclohexyl)aminosulphonyl]biphenyl
(98) 4-amidino-4'-[N-(4-methoxycarbonylcyclohexyl)-N-methylaminocarbonyl]biphenyl hydrochloride
Melting point: 295–300° C.
(99) 4-amidino-4'-[N-(3-methoxycarbonylpropyl)-N-methylaminocarbonyl]biphenyl
Melting point: 235–238° C. (decomp.)
(100) 4-amidino-4'-hydroxy-3'-[N-(4-methoxycarbonylcyclohexyl)-N-methyl-aminocarbonyl)]- biphenyl
Melting point: from 195° C. (decomp.)
$R_f$ value: 0.12 (silica gel; methylene chloride/methanol= 9:1

EXAMPLE 7

4-Hydrazidino-4'-(5-methoxycarbonylpentyloxy) biphenyl

4-Amidino-4'-(5-methoxycarbonylpentyloxy)biphenyl hydrochloride is reacted with a 30-fold excess of hydrazine in methanol at ambient temperature. The reaction lasts for 3 days.

The following compound is obtained analogously:
(1) 4-(N-methoxy-amidino)-4'-(5-methoxycarbonylpentyloxy)biphenyl
(O-methyl-hydroxylamine hydrochloride and ethyldiisopropylamine are used as base)

EXAMPLE 8

4-(N-Ethoxycarbonylamidino)-4'-[(4-methoxycarbonylmethylpiperidino)carbonyl] biphenyl 0.4 g of 4-amidino-4'-[(4-methoxycarbonylmethylpiperidino)carbonyl]biphenyl hydrochloride and 0.11 ml of ethyl chloroformate in 80 ml of methylene chloride are mixed with 0.1N sodium hydroxide solution, with vigorous stirring, until the pH of the mixture is maintained at 9. The organic phase is separated off and evaporated to dryness.

Yield: 0.27 g (60% of theory), $R_f$ value: 0.60 (silica gel; methylene chloride/ethanol= 9:1)

The following compounds are obtained analogously:
(1) 4-(N-methoxycarbonylamidino)-4'-[(3-methoxycarbonylpropylamino)carbonyl]biphenyl
(2) 4-[(3-benzyloxycarbonylpropyl)aminocarbonyl]-4'-(N-methoxycarbonylamidino)biphenyl
(3) 4-(N-benzyloxycarbonylamidino)-4'-[(3-methoxycarbonylpropyl)aminocarbonyl]biphenyl
(4) 4-(N-ethoxycarbonylamidino)-4'-[(3-methoxycarbonylpropyl)aminocarbonyl]biphenyl
(5) 4-(N-methoxycarbonylamidino)-4'-[(4-methoxycarbonylmethylpiperidino)carbonyl biphenyl $R_f$ value: 0.59 (silica gel; methylene chloride/ethanol= 9:1)

(6) 4-(N-benzyloxycarbonylamidino)-4'-[(4-methoxycarbonylmethylpiperidino)carbonyl]biphenyl Melting point: 139–142° C.

$R_f$ value: 0.66 (silica gel; methylene chloride/methanol= 9:1)

(7) 4-(N-ethoxycarbonylamidino)-4'-[(4-ethoxycarbonylmethylpiperidino)carbonyl]biphenyl Melting point: 126–130° C.

$R_f$ value: 0.57 (silica gel; methylene chloride/ethanol= 9:1)

(8) 4-(N-benzyloxycarbonylmethylpiperidino)carbonyl]-4'-(N-methoxycarbonylamidino)biphenyl Melting point: 126–128° C.

$R_f$ value: 0.63 (silica gel; cyclohexane/ethyl acetate=1:3)

(9) 4-(N-methoxycarbonylamidino)-4'-[(4-methoxycarbonylcyclohexyl)aminocarbonyl biphenyl Melting point: 349–351° C. (decomp.)

(10) 4-(N-methoxycarbonyl-amidino-4'-[N-(4-methoxycarbonyl-cyclo-hexyl)-N-methyl-aminocarbonyl]-biphenyl Melting point: 218–220° C.

EXAMPLE 9

4-Amidino-4'-[(4-methoxycarbonylbutyl)sulphinyl)-biphenyl

Prepared from 4-amidino-4'-(4-methoxycarbonylbutylthio)biphenyl by oxidation with m-chloro-perbenzoic acid in methylene chloride at −20° C. for 15 hours.

The following compounds are obtained analogously:

(1) 4-amidino-4'-[[4-[[2-(1-oxido-thiomorpholino)-ethyl] oxycarbonylmethyl]piperidino)carbonyl]biphenyl (2) 4-amidino-4'-[(3-methoxycarbonylpropyl) sulphinylmethyl]biphenyl (3) 4-amidino-4'-(5-methoxycarbonylpentyloxy)-3'-methylsulphinylbiphenyl

EXAMPLE 10

4-Aminomethyl-4'-[(4-methoxycarbonylmethylpiperidino)-carbonyl) biphenyl hydrochloride 1.89 g of 4-cyano-4'-((4-methoxycarbonylmethylpiperidino)carbonyl]biphenyl are dissolved in 40 ml of methanol to which 2 ml of methanolic hydrochloric acid have been added. Hydrogenation is carried out with hydrogen under 5 bars of pressure at ambient temperature in the presence of 0.4 g of 10% palladium/charcoal. After 2.2 hours the catalyst is filtered off and the filtrate is evaporated down. The residue is purified by chromatography on silica gel (eluant: methylene chloride/methanol=9:1)

Yield: 0.78 g (37% of theory),

Melting point: 188–192° C.

$R_f$ value: 0.57 (silica gel; methylene chloride/methanol= 4:1)

The following compounds are obtained analogously:

(1) 4-aminomethyl-4'-[(4-carboxymethylpiperidino)-carbonyl]biphenyl hydrochloride The compound is formed as a by-product in the mixture described above in a 15% yield.

Melting point: 160–164° C.

$R_f$ value: 0.16 (silica gel; methylene chloride/methanol= 4:1)

(2) 4-aminomethyl-4-[[(4-methoxycarbonylpiperidino)-carbonyl]methyl)biphenyl (3) 4-aminomethyl-4[-[(4-methoxycarbonylmethylpiperidino)methyl]biphenyl (4) 4-aminomethyl-4'-[(4,4-bis-methoxycarbonylmethylpiperidino)carbonyl]biphenyl (5) 4-aminomethyl-4'-methoxy-3'-[(4-methoxycarbonylbutyl)aminosulphonyl biphenyl $R_f$ value: 0.17 (silica gel; methylene chloride/methanol= 15:1)

(6) 4-aminomethyl-4'-methoxy-3'-[(4-methoxycarbonylbutyl)aminocarbonyl]biphenyl (7) 4-aminomethyl-3'-[(4-methoxycarbonylcyclohexyl)-aminocarbonyl biphenyl (8) 4-aminomethyl-4'-hydroxy-3'-[N-(4-methoxycarbonylcyclohexyl)-N-methyl-aminocarbonyl]-biphenyl hydrochloride Melting point: 220° C. (from 160° C. sintering, from 180° C. decomp.)

$R_f$ value: 0.30 (silica gel; methylene chloride/methanol/ concentrated ammonia=9:1:0.1)

(9) 4-aminomethyl-4'-methoxy-3'-((4-methoxycarbonylcyclohexyl)-aminocarbonyl]-biphenyl

EXAMPLE 11

3-(5-Carboxyvalerylamino)-3'-guanidinobiphenyl

Prepared by refluxing 3-amino-3'-[(5-carboxyvaleryl) amino]biphenyl hydrochloride with cyanamide in dioxane for 3 hours.

The following compound is obtained analogously:

(1) 3-guanidino-3'-(5-methoxycarbonylvalerylamino)-biphenyl

EXAMPLE 12

4-Cyano-4'-[[[3-(2-methoxycarbonylethyl)phenyl]-aminocarbonyl]methyl]biphenyl

A solution of 1.4 g of dicyclohexylcarbodiimide in 20 ml of tetrahydrofuran is added dropwise, whilst cooling with ice, to a mixture of 1 g of 4'-cyano-biphenylyl-4-acetic acid, 1.2 g of methyl 3-(3-aminophenyl)propionate, 0.57 g of 1-hydroxy-1H-benzotriazole-hydrate and 100 ml of tetrahydrofuran. The mixture is stirred for a further hour, allowed to come to ambient temperature and the dicyclohexylurea precipitated is filtered off. The filtrate is evaporated down and the residue is purified by chromatography on silica gel (eluant: methylene chloride/methanol=30:1).

Yield: 1.58 g (95% of theory),

Melting point: 166–168° C.

The following compounds are obtained analogously:

(1) 4-cyano-4'-[[3-(2-methoxycartonylethyl)phenyl]-aminocarbonyl]biphenyl

Melting point: 129–132° C.

(2) 4-cyano-4'-([[3-(methoxycarbonylmethyl)phenyl]-aminocarbonylmethyl)]biphenyl Melting point: 142–144° C.

(3) 4-cyano-4'-[[3-(methoxycarbonylmethyl)phenyl]-aminocarbonyl]biphenyl (Dimethylformamide is used as solvent)

Melting point: 148–149° C.

(4) 4-cyano-4'-[(methoxycarbonylmethyloxy)-methylcarbonylamino]biphenyl (5) 4-cyano-4'-[(N-(methoxycarbonylmethyl)-N-methyl-amino]methylcarbonylamino]biphenyl (6) 4-cyano-4'-[(4-methoxycarbonylmethylpiperidino)-carbonyl]biphenyl Melting point: 130–134° C.

(7) 4-cyano-4'-( (3-methoxycarbonylmethylpiperidino)-carbonyl]biphenyl

Melting point: 130–134° C.

(8) 4-cyano-4'-[(3-methoxycarbonylmethylpiperidino)-carbonylmethyl]biphenyl $R_f$ value: 0.71 (silica gel; methylene chloride/ethanol=9.:1)

(9) 4-cyano-41'-[(4-methoxycarbonylmethylpiperidino)-carbonylmethyl]biphenyl

Melting point: 116–118° C.

(10) 4-cyano-4'-[(4-methoxycarbonylbutyl)-aminocarbonyl]biphenyl

Melting point: 148–150° C.

(11) 4-cyano-4'-[[4-(2-methoxycarbonylethyl)-piperazino]carbonyl]biphenyl $R_f$ value: 0.62 (silica gel; methylene chloride/ethanol=9:1)

(12) 4-cyano-4'-[(4-methoxycarbonylmethylpiperazino)-carbonyl]biphenyl

Melting point: 170–172° C.

(13) 4-cyano-4'-[(4-methoxycarbonylcyclohexyl)-aminocarbonyl]biphenyl

Melting point: 273–275° C. (decomp.)

(14) 4-(N-benzyloxycarbonylamidino)-4'-[[[2-benzyloxycarbonyl-1-[[2-(4-methoxyphenyl)ethyl]aminocarbonyl]-ethylamino]carbonylmethyl]aminocarbonyl]biphenyl Melting point: 162–165° C.

In order to prepare 4'-(N-benzyloxycarbonylamidino)-biphenyl-4-carboxylic acid, the starting material used is methyl 4'-cyano-biphenyl-4-carboxylate, which is converted analogously to Example 6 into methyl 4'-amidino-biphenyl-4-carboxylate. The latter is converted into the N-benzyloxycarbonyl derivative by reacting it in a 4:1 mixture of methylene chloride and methanol in the presence of 1N sodium hydroxide solution with benzylchloroformate. The saponification of the methylester to obtain the carboxylic acid is carried out using lithium hydroxide.

Glycyl-aspartic acid-β-benzylester-α-[2-(4-methoxyphenyl)ethyl]amide is prepared by known methods of peptide synthesis, by first condensing β-benzyl-N-tert-butyloxycarbonyl-aspartate with 2-(4-methoxyphenyl)ethylamine, according to Example 15, then removing the protection from the amino function of the aspartic acid part and reacting the product with N-tert-butyloxycarbonyl-glycine, again analogously to Example 15, and again removing the protection.

(15) 4-cyano-4'-hydroxy-3'-(N-(4-methoxycarbonylcyclohexyl)-N-methyl-aminocarbonyl]-biphenyl $R_f$ value: 0.40 (silica gel; cyclo-hexane/ethyl acetate=7:3)

(16) 4-cyano-4'-[N-(4-methoxycarbonyl-cyclohexyl)-N-methyl-aminocarbonyl]-biphenyl Melting point: 218–220° C.

EXAMPLE 13

4-Cyano-4'-(5-ethoxycarbonylpentyloxy)biphenyl 1.95 g of 4-cyano-4'-hydroxy-biphenyl are dissolved in 25 ml of dimethylformamide. 0.44 g of a 55% dispersion of sodium hydride in oil is added to the mixture which has been cooled to 0° C. and the resulting mixture is stirred for 0.5 hours. 1.28 g of 6-bromocaproic acid and a further 10 ml of dimethylformamide are added and the mixture is stirred for 2 hours at ambient temperature. The dimethylformamide is distilled off in vacuo, the residue is triturated with water, the precipitate formed is filtered off and recrystallized from ethanol.

Yield: 2.1 g (62% of theory),

Melting point: sinters from 62° C.

Calculated: C 74.75 H 6.87 N 4.15

Found: 74.40 6.76 4.24

The following compounds are obtained analogously:

(1) 4-cyano-4'-(3-methoxycarbonylpropyloxy)biphenyl

Melting point: 107–108° C.

(2) 4-cyano-4'-(4-methoxycarbonylbutyloxy)biphenyl

Melting point: 97–99° C.

(3) 4-cyano-4'-(5-ethoxycarbonylpentyloxy)-3'-nitro-biphenyl (4) 4-cyano-4'- (4-methoxycarbonylbutylthio)biphenyl (5) 3-chloro-4-cyano-4'-(5-ethoxycarbonylpentyloxy)-biphenyl (6) 4-cyano-4'-(5-ethoxycarbonylpentyloxy)-3-fluorobiphenyl (7) 4-cyano-2',3'-dimethyl-4'-(5-ethoxycarbonyl-pentyloxy)biphenyl (8) 4-cyano-4'-(5-ethoxycarbonylpentyloxy)-3'-trifluoromethylbiphenyl (9) 4-cyano-4'-[[(2-methoxycarbonylethyl)-aminocarbonyl methyloxy]biphenyl (4-cyano-4'-[[[N-(2-methoxycarbonylethyl)-N-methylamino]carbonyl]methyloxy]biphenyl is obtained from 4-cyano-4'-([(2-methoxycarbonylethyl)aminocarbonyl]-methyloxy]biphenyl by methylation with methyliodide)

(10) 4-[2-[N-acetyl-N-(2-methoxycarbonylethylamino)-ethyloxy)-4'-cyano-biphenyl

(11) 4-cyano-4'-(2-[N-(2-methoxycarbonylethyl)-N-methanesulphonylamino]ethyloxy]biphenyl

(12) 4-[2-(N-benzoyl-N-(2-methoxycarbonylethyl)amino]-ethyloxy]-4'-cyano-biphenyl

(13) 4-cyano-4'-[(methoxycarbonylmethylaminocarbonyl)-methyloxy]biphenyl

(14) 4-cyano-4'-[N-[(methoxycarbonylmethylaminocarbonyl)methyl]-N-methylamino]biphenyl (Ethyldiisopropylamine was used as the base)

(15) 4-cyano-4'-[N-[[N-(2-methoxycarbonylethyl)-N-methylamino]carbonyl]-N-methylamino]biphenyl (prepared from 4-cyano-4'-[[(2-methoxycarbonylethyl)-aminocarbonyl]amino]biphenyl by methylation with methyl iodide)

(16) 4-cyano-4'-[[(4-methoxycarbonylpiperidino)-carbonyl]methyloxy]biphenyl

(17) 4-cyano-4-(5-methoxycarbonylpentyloxy)-3'-methylthio]biphenyl

(18) 4-cyano-4'-[N-(3-methoxycarbonylpropionyl)-N-methylamino]biphenyl (prepared from 4-cyano-4'-[(3-methoxycarbonylpropionyl)amino]biphenyl by methylation with methyl iodide)

(19) 4-cyano-4'-(N-(4-methoxycarbonylbutyryl)-N-methylamino]biphenyl (prepared from 4-cyano-4'-[(4-methoxycarbonylbutyrl)-amino]biphenyl by methylation with methyliodide)

(20) 4-cyano-4'-[[N-(3-methoxycarbonylpropyl)-N-methylamino]sulphonyl]biphenyl (prepared from 4-cyano-4'-[(3-methoxycarbonylpropyl)-aminosulphonyl]biphenyl by methylation with methyl iodide)

(21) 4-cyano-4'-[N-(4-methoxycarbonylbutyryl)-N-methylamino]biphenyl (prepared from 4-cyano-4'-(4-methoxycarbonylbutyrylamino]biphenyl by methylation with methyliodide)

(22) 4-cyano-4[[(2-methoxycarbonylethyl)thiomethyl]-carbonyl]biphenyl
(prepared from 4-bromoacetyl-4'-cyano-biphenyl and methyl 3-mercaptopropionate)
(23) 4-cyano-4'-[2-(methoxycarbonylmethylthio)ethyl]-biphenyl
(prepared analogously to (22))
(24) 4-cyano-4'-[(3-methoxycarbonylpropyl)thiomethyl]-biphenyl
(prepared analogously to (22))

EXAMPLE 14

4-Cyano-4'-[[(3-ethoxycarbonylpiperidino)carbonyl]-methyloxy]biphenyl 5.35 g of carbonyldiimidazole are added to a solution of 7.6 g of 4-(carboxymethyloxy)-4'-cyano-biphenyl (prepared from 4-cyano-4'-hydroxy-biphenyl and tert.butyl bromoacetate according to Example 13, but with potassium tert.butoxide as base, and subsequent ester cleaving with trifluoroacetic acid) in 30 ml of tetrahydrofuran and the resulting mixture is stirred for 0.5 hours at ambient temperature. 5.1 ml of ethyl piperidine-3-carboxylate are added and the mixture is stirred for 22 hours at ambient temperature. The tetrahydrofuran is evaporated off, the residue is taken up in ethyl acetate and washed successively with saturated sodium bicarbonate solution, 0.1N hydrochloric acid and water. After evaporation of the organic phase the residue remains as an oil.

Yield: 10.5 g (89% of theory),
Calculated: C 70.39 H 6.16 N 7.14
Found: 70.12 6.45 7.14

The following compounds are obtained analogously:
(1) 4-cyano-4'-[[(4-ethoxycarbonylpiperidino)-carbonyl methyloxy]biphenyl
Melting point: 98–100° C.
(2) 4-cyano-4'-[(4-methoxycarbonylmethylpiperidino)-carbonyl]biphenyl
Melting point: 124–125° C.,
$R_f$ value: 0.61 (silica gel; methylene chloride/ethanol= 1:1)
(3) 4-cyano-4'-[(3-ethoxycarbonylmethylpiperidino)-carbonyl]biphenyl
(4) 4-cyano-4'-[(3-methoxycarbonylmethylpyrrolidino]-carbonyl]biphenyl
(5) 4-cyano-4'-[(4-ethoxycarbonylpiperidino)-carbonylmethyl]biphenyl
(6) 4-cyano-4'-[(3-ethoxycarbonylmethylpiperidino)-carbonylmethyl]biphenyl
(7) 4-cyano-4'-[(3-methoxycarbonylmethylpyrrolidino)-carbonylmethyl]biphenyl
(8) 4-cyano-4'-[(3-ethoxycarbonylpiperidino)-carbonylmethyl]biphenyl
(9) 4-(N-benzyloxycarbonylamidino)-4'-[(4-benzoyloxycarbonylmethyl-4-hydroxy-piperidino]-carbonyl biphenyl
(10) 4-cyano-4'-[(4-methoxycarbonylmethylenepiperidino)carbonyl]biphenyl
(11) 4-cyano-4'-[(4,4-bis-methoxycarbonylmethylpiperidino)carbonyl]biphenyl
(12) 4-cyano-4'-[(4-sulphomethylpiperidino)carbonyl]-biphenyl
(13) 4-cyano-4'-[[4-(5-tetrazolylmethyl)piperidino]-carbonyl]biphenyl

EXAMPLE 1

4-Cyano-4'-[(2-ethoxycarbonylethylamino)carbonyl]-biphenyl

A mixture of 2 g of 4'-cyano-biphenylyl-4-acetic acid, 1.9 ml of N-methyl-morpholine and 100 ml of tetrahydrofuran is cooled to −37° C. and 1.1 ml of isobutyl-chloroformate are added. The mixture is stirred for one hour, 1.3 g of β-alanine-ethylester hydrochloride are added and the resulting mixture is stirred for a further 50 hours at ambient temperature.

The resulting solution is stirred into 300 ml of 0.5 molar potassium hydrogen sulphate solution and extracted with ethyl acetate. The ethyl acetate phase is concentrated by evaporation and ether is added, whereupon the product is obtained in crystalline form.

Yield: 1.1 g.(39% of theory),
Melting point: 132–136° C.

The following compounds are obtained analogously:
(1) 4-cyano-4'-[(3-ethoxycarbonylpropylamino)carbonyl]-biphenyl
(2) 4-cyano-4'-[[(2-ethoxycarbonylethylamino)carbonyl]-biphenyl
(3) 4-cyano-4'-[[N-(3-methoxycarbonyl-2-propenyl)-N-methylamino]carbonyl)biphenyl
(4) 4-[[2-benzyloxycarbonyl-1-[[2-(4-methoxyphenyl)-ethyl]aminocarbonyl]ethylamino]carbonylmethyl]-4'-cyano-biphenyl
(5) 4-cyano-4'-((4-ethoxycarbonylmethylpiperidino)-carbonyl]biphenyl
Melting point: 118–120° C.
(6) 4-cyano-4'-((4-dimethylaminocarbonylmethylpiperidino)carbonyl]biphenyl

EXAMPLE 16

4-Cyano-4'-(4-methoxycarbonylbutyrylamino)biphenyl 6.6 g of 4-amino-4'-cyano-biphenyl (
Melting point: 171–173° C., prepared by reduction of 4-cyano-4'-nitro-biphenyl with hydrogen in the presence of palladium/charcoal in ethyl acetate, 4-cyano-4'-nitro-biphenyl is prepared by reacting 4-cyano-biphenyl with fuming nitric acid) and 5.8 g of N-ethyl-diisopropylamine are dissolved in 70 ml of methylene chloride and 5.6 g of glutaric acid monomethylester chloride are added with stirring. The mixture is stirred for two hours at ambient temperature. The organic phase is washed successively with 0.1N sodium hydroxide solution, 0.1N hydrochloric acid and water. After evaporation of the organic phase the residue is recrystallized from ethanol.

Yield: 7.5 g (68% of theory),
Melting point: 153–155° C.

The following compounds are obtained analogously:
(1) 3-amino-3'-(5-methoxycarbonylvalerylamino)biphenyl
(2) 3-bromo-4'-cyano-4-(4-methoxycarbonylbutyrylamino)-biphenyl
(This compound may also be obtained by bromination of 4-cyano-4'-(4-methoxycarbonylbutyrylamino)biphenyl with bromine in glacial acetic acid)
(3) 4-cyano-3',5'-dibromo-4'-(4-methoxycarbonylbutyrylamino)biphenyl
(4) 3-acetylamino-4'-cyano-4-(5-methoxycarbonylpentyloxy)biphenyl
(5) 3-benzoylamino-4'-cyano-4-(5-methoxycarbonylpentyloxy)biphenyl
(6) 4-cyano-3'-methanesulphonylamino-4'-(5-methoxycarbonylpentyloxy)biphenyl
(7) 3-benzenesulphonylamino-4'-cyano-4-(5-methoxycarbonylpentyloxy)biphenyl (8) 4-cyano-4'-[(3-methoxycarbonylpropyl)-aminosulphonyl)biphenyl (9) 4-cyano-4'-methoxy-3'-[(4-methoxycarbonylbutyl)-aminosulphonyl]biphenyl (Prepared from the trimethylsilyl-5-trimethylsilylaminovalerate produced as an intermediate product and subsequent esterification with methanolic hydrochloric acid)

$R_f$ value: 0.31 (silica gel; methylene chloride/methanol=15:1)

EXAMPLE 17

4-Cyano-4'-[(4-methoxycarbonylbutyl)sulphonyl]biphenyl

At 90° C, 30% hydrogen peroxide is slowly added to a solution of 4-cyano-4'-(4-methoxycarbonyl-butylthio)-biphenyl in a 10:6 mixture of acetic anhydride and glacial acetic acid. The mixture is stirred for another hour, poured onto ice water, neutralized and extracted with ethyl acetate. The ethyl acetate phases are evaporated down and the residue is purified by column chromatography.

The following compounds are obtained analogously:
(1) 4-cyano-4'-[(3-methoxycarbonylpropyl)-sulphonylmethyl]biphenyl
(2) 4-cyano-4'-(5-methoxycarbonylpentyloxy)-3'-methylsulphony]biphenyl

EXAMPLE 18

3-Amino-4'-cyano-4-(5-methoxycarbonylpentyloxy)biphenyl

Prepared from 4-cyano-4'-(5-methoxycarbonyl-pentyloxy)-3'-nitro-biphenyl by hydrogenating with hydrogen under 5 bars of pressure in methanol in the presence of 10% palladium/charcoal at ambient temperature.

EXAMPLE 19

4-Cyano-4'-[(4-methoxycarbonylmethylpiperidino)-methyl]-biphenyl,

Prepared by alkylating methyl piperidyl-4-acetate with 4-bromomethyl-4b-cyano-biphenyl in dimethyl-formamide in the presence of dusopropylethylamine.

The following compounds are obtained analogously:
(1) 4-cyano-4'-[(3-methoxycarbonylmethylpiperidino)-methyl]biphenyl
(2) 4-cyano-4'-[2-(4-methoxycarbonylpiperidino)ethyl]-biphenyl
(3) 4-cyano-4'-[2-(3-methoxycarbonylmethylpiperidino]-ethyl-biphenyl
(4) 4-cyano-4'-[(3-methoxycarbonylmethylpyrrolidino)-methyl]biphenyl
(5) 4-cyano-4'-[2-(3-methoxycarbonylmethylpyrrolidino)-ethyl]biphenyl
(6) 4-cyano-4'-[2-(3-methoxycarbonylpiperidino)ethyl]-biphenyl

EXAMPLE 20

4-Cyano-4'-[(2-ethoxycarbonylethylaminocarbonyl)amino]-biphenyl

Prepared by reacting 4-amino-4'-cyano-biphenyl with ethyl 3-isocyanato-propionate in dioxane at 50° C.

EXAMPLE 21

4-Cyano-4'-[(2-ethoxycarbonylethyl)amino-sulphonylamino]biphenyl 0.68 g of 4-amino-4'-cyano-biphenyl and 1.1 g of 2-[(2-ethoxycarbonylethyl)aminosulphonyloxy]phenol are heated in 5 ml of dimethylformamide to 80° C. for 15 hours. The dimethylformamide is distilled off in vacuo and the residue is taken up in ethyl acetate. After washing with water, the organic phase is evaporated down and the residue remaining is purified by column chromatography (silica gel; eluant: cyclohexane/ethyl acetate=7:3).

Yield: 0.8 g (62% of theory), $R_f$ value: 0.19 (silica gel; cyclohexane/ethyl acetate=7:3)

EXAMPLE 22

| Dry ampoule containing 2.5 mg of active substance per 1 ml | |
|---|---|
| Composition: | |
| Active substance | 2.5 mg |
| Mannitol | 50.0 mg |
| Water for injections ad | 1.0 ml |

Preparation:

The active substance and mannitol are dissolved in water. After transferring the solution to the ampoule, it is freeze-dried.

At the point of use, the solution is made up with water for injections.

EXAMPLE 23

| Dry ampoule containing 35 mg of active substance per 2 ml | |
|---|---|
| Composition: | |
| Active substance | 35.0 mg |
| Mannitol | 100.0 mg |
| Water for injections ad | 2.0 ml |

Preparation:

The active substance and mannitol are dissolved in water. After transferring the solution to the ampoule, it is freeze-dried.

At the point of use, the solution is made up with water for injections.

EXAMPLE 24

| Tablet containing 50 mg of active substance | |
|---|---|
| Composition: | |
| (1) Active substance | 50.0 mg |
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granules. From this mixture, compressed tablets are produced, biplanar, facetted on both sides and notched on one side. Diameter of tablets: 9 mm.

EXAMPLE 25

Tablet containing 350 mg of active substance

Composition:

| | |
|---|---|
| (1) Active substance | 350.0 mg |
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granules. From this mixture, compressed tablets are produced, biplanar, facetted on both sides and notched on one side. Diameter of tablets: 12 mm.

EXAMPLE 26

Capsules containing 50 mg of active substance

Composition:

| | |
|---|---|
| (1) Active substance | 50.0 mg |
| (2) Dried corn starch | 58.0 mg |
| (3) Powdered lactose | 50.0 mg |
| (4) Magnesium stearate | 2.0 mg |
| | 160.0 mg |

Preparation:

(1) is triturated with (3). This triturate is added to the mixture of (2) and (4), with thorough mixing.

This powdered mixture is packed into size 3 hard gelatin oblong capsules in a capsule filling machine.

EXAMPLE 27

Capsules containing 350 mg of active substance

Composition:

| | |
|---|---|
| (1) Active substance | 300.0 mg |
| (2) Dried corn starch | 46.0 mg |
| (3) Powdered lactose | 30.0 mg |
| (4) Magnesium stearate | 4.0 mg |
| | 430.0 mg |

Preparation:

(1) is triturated with (3). This triturate is added to the mixture of (2) and (4), with thorough mixing.

This powdered mixture is packed into size 0 hard gelatin oblong capsules in a capsule filling machine.

What is claimed is:

1. A biphenyl compound of formula

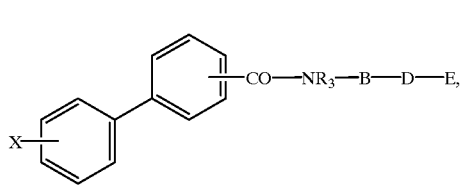

(I)

wherein one of the rings of the biphenyl moiety is optionally mono- or disubstituted by R1 and the other is optionally mono- or disubstituted by R2, wherein $R_1$ and $R_2$, which may be identical or different, represent halogen atoms, alkyl, hydroxy, trifluoromethyl, amino, nitro, alkoxy, alkylsulphenyl, alkylsulphinyl, alkylsulphonyl, alkylcarbonylamino, N-alkyl-alkylcarbonylamino, arylcarbonylamino, N-alkylarylcarbonylamino, alkylsulphonylamino, N-alkylalkylsulphonylamino, arylsulphonylamino or N-alkylarylsulphonylamino groups, wherein the aryl moiety is a phenyl ring which can be mono-, di- or trisubstituted by halogen atoms, hydroxy, amino, alkyl, alkoxy, alkylsulphenyl, alkylsulphinyl, alkylsulphonyl, alkylcarbonylamino and alkylsulphonylamino groups and each alkyl moiety has 1 to 3 carbon atoms, or $R_1$ and $R_2$ each represent a naphthyl ring;

$R_3$ represents a hydrogen atom or an optionally phenyl-substituted $C_{1-3}$-alkyl group, wherein the phenyl group may be mono or disubstituted by the above-mentioned groups $R_1$ and $R_2$;

B represents a cyclohexylene group optionally mono-, di or trisubstituted by halogen atoms, amino, hydroxy, $C_{1-3}$-alkyl or $C_{1-3}$-alkoxy groups;

X represents an amino ($C_{1-3}$-alkyl) or amidino group, wherein one of the hydrogen atoms at one of the nitrogen atoms in the above-mentioned groups is optionally replaced by a $C_{1-4}$-alkyl, $C_{2-5}$-(alkoxycarbonyl) or phenyl($C_{1-3}$-alkoxy)carbonyl group, wherein the above-mentioned phenyl groups is optionally mono- or disubstituted by the above-mentioned groups $R_1$ and $R_2$;

D represents a bond, a straight-chained or branched $C_{1-4}$-alkylene group which is optionally mono- or poly-unsaturated; and E represents a carboxy group or a $C_{2-6}$(alkoxycarbonyl) group wherein the alkoxy moiety can be substituted in the 1-, 2- or 3-position by a phenyl group (which is optionally mono- or disubstituted by the above-mentioned groups $R_1$ and $R_2$);

a stereoisomer thereof, a mixture of stereoisomers or a pharmaceutically acceptable salt thereof with an inorganic or organic acid or base.

2. The biphenyl compound as recited in claim 1, wherein one of the rings of the biphenyl moiety is optionally be substituted by $R_1$ and the other is optionally substituted by $R_2$, wherein $R_1$ and $R_2$, which may be identical or different, represent fluorine, chlorine or bromine atoms, $C_{1-3}$-alkyl, hydroxy, trifluoromethyl, amino, nitro, $C_{1-3}$-alkoxy, $C_{1-3}$-alkylsulphenyl, $C_{1-3}$-alkylsulphinyl, $C_{1-3}$-alkylsulphonyl, $C_{1-3}$-alkylcarbonylamino, benzoylamino, $C_{1-3}$-alkylsulphonylamino or phenyl-sulfonylamino groups;

or one of the rings of the biphenyl moiety is disubstituted by $R_1$ and the other by $R_1$, wherein $R_1$ and $R_2$, which may be identical or different, represent $C_{1-3}$-alkyl groups chlorine or bromine atoms;

$R_3$ represents a hydrogen atom or a $C_{1-3}$-alkyl group;

B represents a cyclohexylene;

X represents an aminomethyl or amidino group, whilst one of the hydrogen atoms at one of the nitrogen atoms in the above-mentioned groups is optionally replaced by a $C_{2-5}$-(alkoxycarbonyl), benzyloxycarbonyl, 1-phenylethoxycarbonyl or 2-phenylethoxycarbonyl group;

D represents a bond, a straight-chained or branched $C_{1-4}$-alkylene group; and E represents a carboxy group or a $C_{2-6}$(alkoxycarbonyl) group, wherein the alkoxy moiety is optionally substituted in the 1-, 2- or 3-position by a phenyl group;

a stereoisomer thereof, a mixture of stereoisomers, or a pharmaceutically acceptable salt thereof with organic and inorganic acid or base.

3. The biphenyl compound as recited in claim 1, wherein the phenyl group linked to the group X is optionally substituted by a fluorine, chlorine or bromine atom, and the phenyl ring linked to the group —CO— is optionally substituted by a fluorine or chlorine atom or by a hydroxy, methoxy, trifluoromethyl, methylsulphenyl, methylsulphinyl, methylsulphonyl, nitro, amino, acetylamino, benzoylamino, methanesulphonylamino or benzenesulphonylamino group, or the phenyl ring linked to group —CO— is substituted by one or two methyl groups or by one or two bromine atoms;

$R_3$ represents a hydrogen atom or a methyl group;

B represents a cyclohexylene;

X represents an amidino group, wherein a hydrogen atom at one of the nitrogen atoms in the above-mentioned groups is optionally replaced by a methoxycarbonyl, ethoxycarbonyl or benzyloxycarbonyl group;

D represents a bond, a straight-chained or branched $C_{1-3}$-alkylene group; and E represents a carboxy group or a $C_{2-5}$(alkoxycarbonyl) group, wherein the alkoxy moiety is optionally substituted in the 1- or 2-position by a phenyl group;

a stereoisomer thereof, a mixture of stereoisomers, or a pharmaceutically acceptable salt thereof with organic and inorganic acid or base.

4. The biphenyl compound as recited in claim 1, wherein the phenyl group linked to the group X is unsubstituted and the phenyl ring linked to the group CO is optionally substituted by a hydroxy or methoxy group;

$R_3$ represents a hydrogen atom or a methyl group;

B represents a cyclohexylene;

X represents an amidino group, wherein a hydrogen atom at one of the nitrogen toms in the above-mentioned group is optionally replaced by a methoxycarbonyl, ethoxycarbonyl or benzyloxycarbonyl group;

D represents a bond, a methylene or ethylene group; and

E represents a carboxy, methoxycarbonyl, ethoxycarbonyl or benzyloxycarbonyl group;

a stereoisomer thereof, a mixture of stereoisomers, or a pharmaceutically acceptable salt thereof with organic and inorganic acid or base.

5. The biphenyl compound as recited in claim 4, wherein the biphenylyl group is unsubstituted;

$R_3$ represents a hydrogen atom or a methyl group;

B represents a cyclohexylene group;

X represents an amidino group;

D represents a bond; and

E represents a carboxy, methoxycarbonyl, ethoxycarbonyl or benzyloxycarbonyl group;

a stereoisomer thereof, a mixture of stereoisomers, or a pharmaceutically acceptable salt thereof with organic and inorganic acid or base.

6. The biphenyl compound as recited in claim 4, 4-amidino-4'-[(4-carboxycyclohexyl)aminocarbonyl] biphenyl;

or a pharmaceutically acceptable salt thereof with inorganic or organic acid or base.

7. The biphenyl compound as recited in claim 4, 4-amidino-4'-[(4-methoxycarbonylcyclohexyl) aminocarbonyl]biphenyl;

or a pharmaceutically acceptable salt thereof with inorganic or organic acid or base.

8. A pharmaceutical composition of matter comprising a biphenyl compound as recited in claim 1 and a pharmaceutically acceptable carrier or excipient.

9. A method for treating or preventing diseases selected from venous and arterial thrombosis, cerebrovascular diseases, lung embolism, cardiac infarction or arteriosclerosis in a warm blooded animal which comprises administering to said animal in a need thereof a therapeutically effective amount of a biphenyl compound as recited in claim 1.

* * * * *